US 11,766,491 B2

(12) United States Patent
Lim

(10) Patent No.: US 11,766,491 B2
(45) Date of Patent: Sep. 26, 2023

(54) AIR-WATER-FOOD-FABRIC-SPACE-UTILITY SANITIZER

(71) Applicant: Hyeonjoo Lim, Valencia, CA (US)

(72) Inventor: Hyeonjoo Lim, Valencia, CA (US)

(*) Notice: Subject to any disclaimer, the term of this patent is extended or adjusted under 35 U.S.C. 154(b) by 307 days.

(21) Appl. No.: 15/929,421

(22) Filed: May 1, 2020

(65) Prior Publication Data

US 2021/0338857 A1 Nov. 4, 2021

(51) Int. Cl.
*A61L 2/10* (2006.01)
*A23L 3/28* (2006.01)
(Continued)

(52) U.S. Cl.
CPC ............... *A61L 2/10* (2013.01); *A01M 1/04* (2013.01); *A23L 3/28* (2013.01); *A61L 2/26* (2013.01); *A61L 9/20* (2013.01); *B01D 53/1475* (2013.01); *B01D 53/1487* (2013.01); *B09C 1/00* (2013.01); *C02F 1/32* (2013.01); *A01M 2200/012* (2013.01); *A61L 2202/11* (2013.01); *A61L 2202/122* (2013.01); *A61L 2202/26* (2013.01);
(Continued)

(58) Field of Classification Search
None
See application file for complete search history.

(56) References Cited

U.S. PATENT DOCUMENTS

| 6,403,030 B1 * | 6/2002 | Horton, III | ............ | C02F 1/325 |
| | | | | 210/748.11 |
| 6,494,940 B1 | 12/2002 | Hak | | |

(Continued)

FOREIGN PATENT DOCUMENTS

| CA | 2 137 863 C | 5/2007 |
| EP | 2 377 608 A1 | 10/2011 |

(Continued)

OTHER PUBLICATIONS

Mims, S.A. et al. (2004), "Fungal spores are transported long distances in smoke from biomass fires". Atmospheric Environment 38:651-5.

(Continued)

*Primary Examiner* — Andrew Smyth

(57) ABSTRACT

An Air-Water-Food-Fabric-Space-Utility sanitizer (all in one) comprises a detachable blower chamber, a detachable UVC lamp holder, a detachable UVC lamp chamber, a detachable water chamber and a detachable lid. Said invention transforms to an air purifier, a chamber-style sanitizer, or a stand-style sanitizer when one or more chambers are detached. Germicidal lamps surround a target such as air, water, food (meats, plants), fabric (masks, towels), space, utility and soil to kill pests, parasites, insects and pathogenic spores. Said invention also develops seed germination. Water converts gas (MVOC) to liquid and arrests airborne contaminants. A blower drives them to water to enable the use of optimal dosage of UVC light. By either UVC-irradiating water or oxidizing water, pathogens are destroyed in the water chamber. Filters activate spore dispersal when disposed by burning. By not using potentially hazardous waste or an air outlet, pathogenic spores cannot reproduce or return to the environment.

8 Claims, 19 Drawing Sheets

(51) Int. Cl.
*C02F 1/32* (2023.01)
*B01D 53/14* (2006.01)
*A61L 2/26* (2006.01)
*A61L 9/20* (2006.01)
*B09C 1/00* (2006.01)
*A01M 1/04* (2006.01)

(52) U.S. Cl.
CPC ..... *A61L 2209/12* (2013.01); *B01D 2252/103* (2013.01); *C02F 2201/004* (2013.01); *C02F 2201/3227* (2013.01); *C02F 2303/04* (2013.01)

(56) References Cited

U.S. PATENT DOCUMENTS

| | | | |
|---|---|---|---|
| 6,955,715 B1* | 10/2005 | Tittle | B01D 47/021 96/351 |
| 7,347,888 B2 | 3/2008 | Hecker et al. | |
| 7,361,904 B2* | 4/2008 | Cassassuce | C02F 9/20 250/436 |
| 7,727,406 B2 | 6/2010 | Lam | |
| 8,226,887 B2 | 7/2012 | Harmon et al. | |
| 8,399,869 B2 | 3/2013 | Rosier et al. | |
| 10,410,853 B2 | 9/2019 | Stibich et al. | |
| 2004/0076568 A1 | 4/2004 | Yan et al. | |
| 2008/0067414 A1* | 3/2008 | Cassassuce | C02F 1/325 250/435 |
| 2015/0202107 A1 | 7/2015 | Khan | |

FOREIGN PATENT DOCUMENTS

| | | |
|---|---|---|
| EP | 2 174 670 B1 | 4/2013 |
| WO | 01/068222 A1 | 9/2001 |
| WO | WO 01/068222 A1 | 9/2001 |

OTHER PUBLICATIONS

Health Technology Assessment Unit Medical Development Division Ministry Of Health 015/06 (2006), "Plasmacluster Ion" In Technology Review Oct. 2016.

Markland, S. et al. (2016), "Bacillus cereus Mechanisms of Resistance to Food Processing" in "The Diverse Faces of Bacillus cereus" edited by Savini, V.

Norton, E. (2013),"Which Parent Do Fungi Take After?" American Association for the Advancement of Science, in Jane L. "The Silent War Within: Biochemisry & Legal Research on Parasitic Fungi".

Data Source: Ultra-Violet Products Ltd. (2020), "HEPA/UV3 PCR Workstation and Cabinet Installation and User Instructions".

Jane L. (2014), "The Silent War Within: Biochemistry & Legal Research on Parasitic Fungi". pp. 168, 290, & 356.

Rudolf E. N. (2002),"Effects of UV-irradiation on seed germination". Sci Total Environ. 299(1-3), 173-6 doi: 10.1016/s0048-9697(02)00232-2.

* cited by examiner

AIR-WATER-FOOD-FABRIC-SPACE-UTILITY SANITIZER

BACKGROUND OF THE INVENTION

Neither charcoal filters nor HEPA filters destroy pathogenic spores. Due to the thickness and density of HEPA filters of prior apparatuses, the blowers thereof have been noisy and ineffective. HEPA filters are not reusable thereby producing hazardous waste because pathogenic spores multiply by fire-induced convection and radiation when filters are disposed by burning.

The common assumption that plant pathogens are killed by burning was contradicted by the spread of Karnal bunt (a fungal disease of wheat) to surrounding fields when wheat infected with *T. indica* is burned (Roux and O'Brien, 2001). Many fungal spores in smoke from all test fires, and from large fires in Yucatan more than 1500 km distant, suggest that plant pathogens might be spread considerably farther than surrounding fields [1].

Ozone generators, ion precipitators, plasmacluster ion (PCI) and photocatalytic oxidation (PCO) technologies have been criticized for an incomplete process or side effects.

Health Technology Assessment Unit Medical Development Division Ministry of Health reported in its technology review published in October, 2006, "It was claimed by the vendor that PCI technology was 99 percent effective in killing-off the bird flu virus in a controlled environment, also again 26 other kinds of harmful airborne substances, including bacteria, mould fungi, viruses and allergens. There is no scientific evidence to support the use of plasmacluter ion technology in eliminating the airborne bird-flu virus as claimed in the advertisement [2]."

PCO technology chemically manufactures ions using UV radiation shined onto either a photocatalyst, titanium dioxide (TiO2), or a combination of TiO2 and other metals, to create a catalytic reaction. The byproducts include undesirable gas such as carbon dioxide.

Ion generators (ozone generators) release ions into the surrounding area. The charged particles are attracted to the surfaces such as curtains and walls, or other airborne particles floating in the air and then fall onto the floor, which makes the surfaces become dirtier. Since they target only particles not gasses, volatile organic compounds (VOCs) including formaldehydes are not removed by ion-using cleaners.

Water-using air cleaners without a germicidal capacity cause pathogenic spores to germinate. Germinated pathogens change their forms to spores when the air is dehumidified without a sanitizing process, thereby causing more problems than solutions.

Prior apparatuses use water as a filter without using ionizing UVC light. They have been complained for bad odor as a result of microbial germination.

Aqueous ozone has a higher potential than most oxidizing agents to inactivate spores. Studies involving the inactivation of spores by oxidizing agents suggest that inactivation is a result of oxidative damage to the spores' inner membrane. Spores have been shown to be inactivated by several oxidizing agents, including chlorine dioxide, hydrogen peroxide, organic hydroperoxides, "ozone", and sodium hypochlorite (bleach). Spores of *B. subtilis* were more easily inactivated, did not germinate with nutrient germinants, and did not cause release of DPA (Ca-DiPicolinic Acid) from the spores' inner core [3].

Fungi use sexual reproduction not just to mix up already existing genetic diversity, but also to actually produce it from scratch. *Cryptococcus neoformans* causes about 600,000 deaths worldwide every year [4].

Prior apparatuses have relied solely upon five incorrect assumptions that pathogenic spores will not reproduce, will not germinate, or will not return to the environment:

(a) if they are entrained by HEPA filters;

(b) if hazardous filters are disposed by burning;

(c) if they are irradiated quickly by a UVC lamp;

(d) if filters are replaced with water; and (e) if generated ions ionize them.

The common assumption that only ionizing radiation will cause harms to live organisms is contradicted. Non-ionizing radiation (electromagnetic field-EMF) is also a threat to humans and animals since it "fosters" spore dispersal while ionizing radiation such as UVC light "destroys" them.

Dosages for a 90% destruction of most pathogens range from 2,000 to 8,000 $\mu W \cdot s/cm^2$. A fungus *Aspergillus niger* will not die unless 330,000 $\mu W \cdot s/cm^2$ (microwatt seconds per square centimeters) is used [5]. However, UV bulbs provide only 300-1000 μW per inch (762-2,540 μW per centimeter). Distance and duration are the major factors to determine a lethal dosage. Unless a lethal dosage (short distance and long hours) is applied, pathogens do not die.

The most recent study of Dr. David Brenner M.D., revealed that far UVC cannot go past tear layers and top layer of skin while UVB light or UVA light causes cataracts (eye disease) and damages skin.

Blood is irradiated by UVC light to treat leukemia (blood cancer) (Jane L. 2014, The Silent War Within: Biochemistry & Legal Research on Parasitic Fungi, p. 290) because the chemical element (iron as a photoreceptor) of blood can absorb UVC light that destroys parasitic pathogens in blood (Id. p. 168) [6]. Unless UVC lamps are close enough (within 6 inches from the lamp), UVC light cannot affect human skin tissues.

Although many UVC lamps and lamp holders are sold in the market, those products have no means to drive airborne contaminants to a chamber in order to apply effective dosages of UVC light.

Prior apparatuses do not provide sufficient dosage not only because they allow entrained contaminants to leave their germicidal chambers as soon as they enter thereto but also because L-type fused quartz UVC lamp doped with titanium is not capable of decomposing molecules. Prior apparatuses have no means to seize airborne pathogens for the duration required to destroy pathogens.

Prior apparatuses are not designed for easy cleaning while remnants of contaminants are accumulated in the air pathways.

Prior apparatuses do not transform in order to sanitize multiple elements such as air, water, food, fabric, space, household utility, and soil thereby requiring users to purchase multiple apparatuses such as an air purifier, a UV wand, a UV chamber, etc.

Prior wand-style UV apparatuses are difficult to use because users get tired of holding them until the job is done.

Prior wand-style and stand-style UV apparatuses are not effective in irradiating household items because targets receive UV light only in one side unless users reposition them multiple times. For example, a book has six sides that need to be irradiated thereby making users change the direction of the apparatus or the book five more times to ensure that all sides are irradiated.

Prior apparatuses that purify water in water pipes do not effectively irradiate water. Those apparatuses position water around a UVC lamp inserted inside a pipe while the UVC lamp should surround water. They also fail to arrest water for the adequate dosages of UVC light to be applied in one place because they have no means to keep water in one place for the duration to kill pathogens.

Prior ion-generating apparatuses have no means to block EMFs.

UV light sped the germination of seeds [7]. If UVC lamps and holders are readily available at home, home gardeners will utilize them to enhance germination of seeds or to destroy soil fungi instead of purchasing additional apparatuses.

FIELD OF THE INVENTION

This disclosure relates to a multifunctional sanitizer that entrains, converts, removes or destroys contaminants including:
(a) particles (dust, pollen);
(b) pathogenic spores from bacteria, fungi, viruses;
(c) harmful gas (carbon dioxide, cigarette smoke, microbial volatile organic compounds);
(d) pests;
(e) parasites; and
(f) insects (flies, mosquitoes, dust mites, mosses)
in air, water, food (meats and plants), fabric, space, household utility, soil, etc.

BRIEF SUMMARY OF THE INVENTION

Air-Water-Food-Fabric-Space-Utility sanitizer comprises:
(a) a detachable blower chamber to which a power cord is attached;
(b) a detachable UVC lamp holder to which a power cord and a ballast are attached;
(c) a plurality of UVC lamps;
(d) a detachable UVC lamp chamber;
(e) a detachable water chamber; and
(f) a detachable disk-shaped lid.

Said invention solves all problems of prior apparatuses depicted in the background of said invention and provides the following advantages.

Said invention entrains, converts, removes or destroys various contaminants such as pathogenic spores, harmful gas, pests, parasites, and insects in multiple elements such as air, water, food, fabric, space, household utility, soil, etc.

Depending on the target to sanitize, said invention easily transforms to three types of sanitizer. When all compartments are used, said invention serves as an air purifier. When the blower chamber is detached, said invention transforms to a chamber-style sanitizer. When all three chambers are detached, said invention transforms to a stand-style sanitizer. Said invention is the first apparatus that can transform.

Said invention ensures enough time to destroy pathogens by using irradiated water or oxidized water from which pathogens cannot escape.

Said invention does not reproduce or circulate infectious contaminants because it does not have an outlet.

Said invention does not produce hazardous waste because it does not have a HEPA filter. Said invention uses irradiated or oxidized water as a filter or a pathogen killer.

Unlike prior apparatuses that cause 'spore dispersal' through the air pressure received by their filters blown by their blowers, said invention deactivates 'spore dispersal' because it uses water irradiated by UVC lamps that are capable of forming aqueous ozone nearby the surface of water in the water chamber. Ozone produced by any means other than UVC light does not destroy pathogens. In order to be effective in killing pathogens, ozone should be a result after UVC light was irradiated to the targeted air. Ozone is not a cause to kill pathogens. Spore dispersal is activated by non-ionizing radiation (EMF) or convection if aqueous ozone or UVC light is not present. Either aqueous ozone or ozone is formed when UVC irradiates water molecules and oxygen atoms in the water chamber wherein UVC lamps surround the water chamber and irradiate the water. UV-irradiation of aqueous ozone produces hydrogen peroxides which may initiate decomposition of additional ozone to $OH^-$ radical. Ozone decomposition leads to the formation of $OH^-$ radical which is an effective oxidizer.

Unlike prior apparatuses that cause 'spore dispersal' through the air pressure received by their filters blown by their blowers, said invention deactivates 'spore dispersal' because it also uses oxidized water as an alternative method to filter or to kill pathogens. Spore dispersal is activated by oxygen driven from a blower if an oxidizer is not present.

Unlike prior apparatuses that use water as a filter, said invention deactivates 'spore germination' because its UVC lamps kill pathogens. Spore germination is activated by water if adequate dosages of UVC light are not applied to the water used as a filter.

Said invention provides two options to sterilize water. Said invention sterilizes water either by UVC light or by an oxidizer, which means pathogenic germination does not occur if water is timely sterilized and disposed.

Said invention, by using water, removes harmful gas such as formaldehyde (MVOC), carbon dioxide, and cigarette smoke. Water dissolves gas by converting gaseous molecules to aqueous molecules.

Said invention uses a transparent material for housing. Quartz glass not only benefits from germicidal photons emitted from the UVC chamber but also indicates when to replace UVC lamps, when to renew used water, when to clean the compartments, and when to clean the air passage. These indicators are paramount to air purifiers or sanitizers. The transparent housing has not been available for prior apparatuses due to the misconception that UV light causes cancer while "infected blood is irradiated by the UV light before blood transfusions." (Id. p. 356) [6]. Therefore, said invention is the first apparatus using a transparent material for housing in this field.

Said invention does not require users' timely efforts to hold or to reposition a target to sanitize. Said invention emits UVC light from all directions (360°) because it places a target in the center of the cylindrically shaped UVC lamp chamber wherein multiple lamps surround the target. Even sunlight cannot provide this benefit because sunlight casts a shadow in the other side of a target to sanitize. Said invention is the first apparatus that allows multiple UVC lamps to surround a target.

Said invention provides a method to limit EMFs since it uses water as a catalyst to convert gas to liquid and it uses water as a filter to arrest airborne contaminants. Water blocks radiation (EMF), which is a reason for bad Wi-Fi connections or for impaired security IR sensors during the rainy season. In result, said invention prevents EMF-induced spore dispersal while the water in the water chamber cools the UVC lamp chamber wherein the water chamber is coaxially positioned.

DETAILED DESCRIPTION OF THE INVENTION

Figure 1:
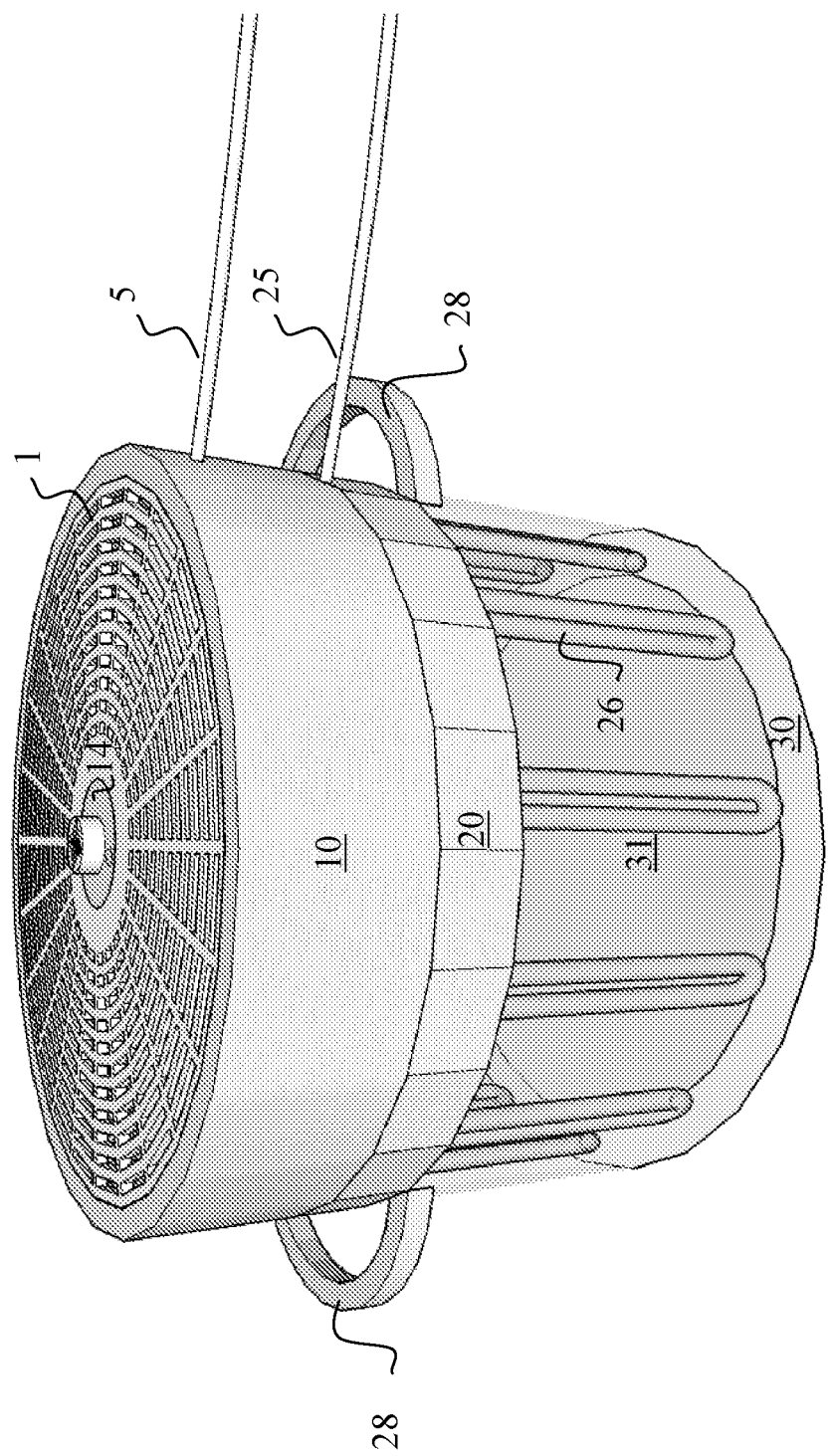
FIG. 1 is a perspective top and front view of the Air-Water-Food-Fabric-Space-Utility Sanitizer.
Figure 2:
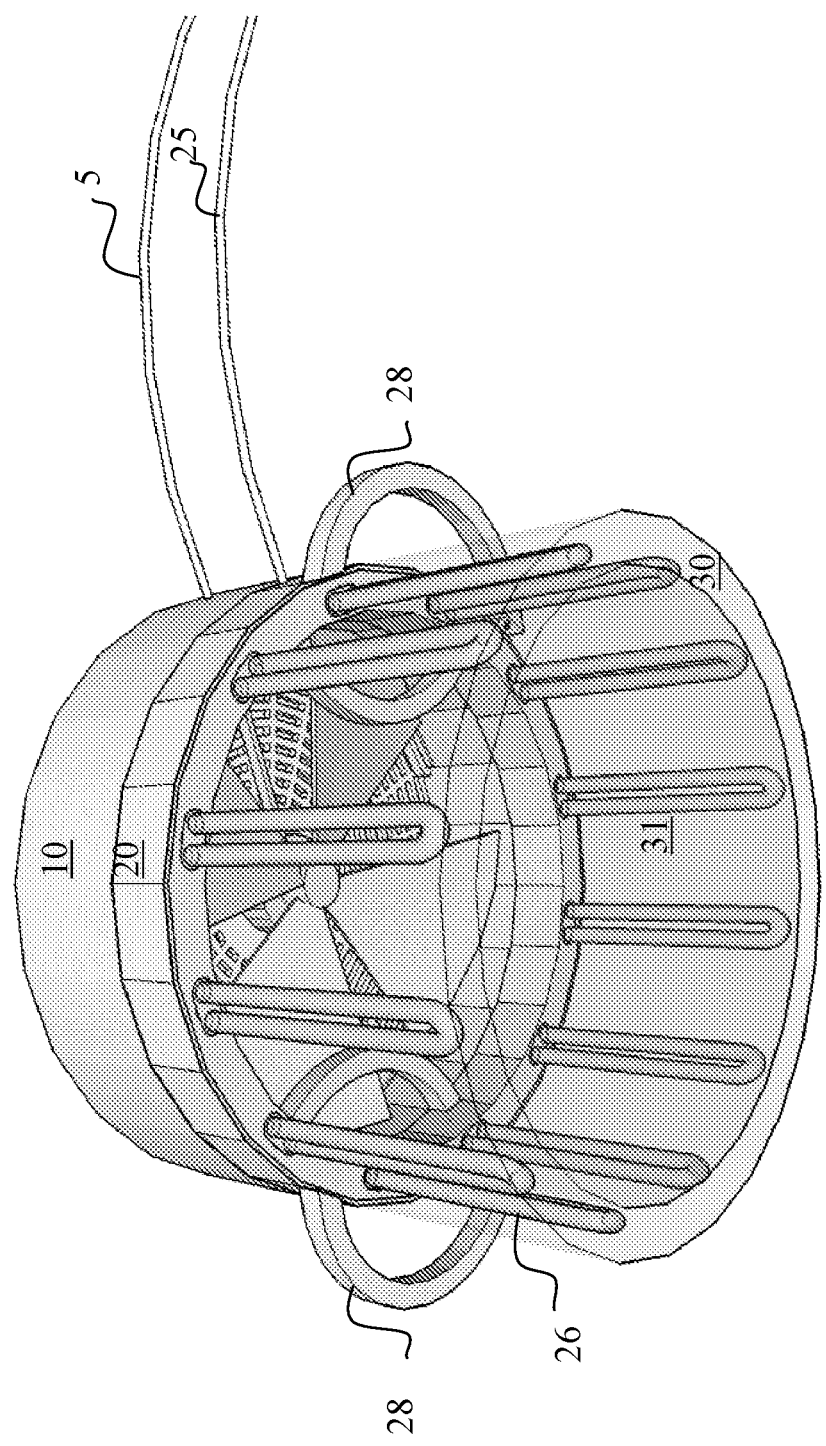
FIG. 2 is a perspective bottom and front view of FIG. 1.
Figure 3:
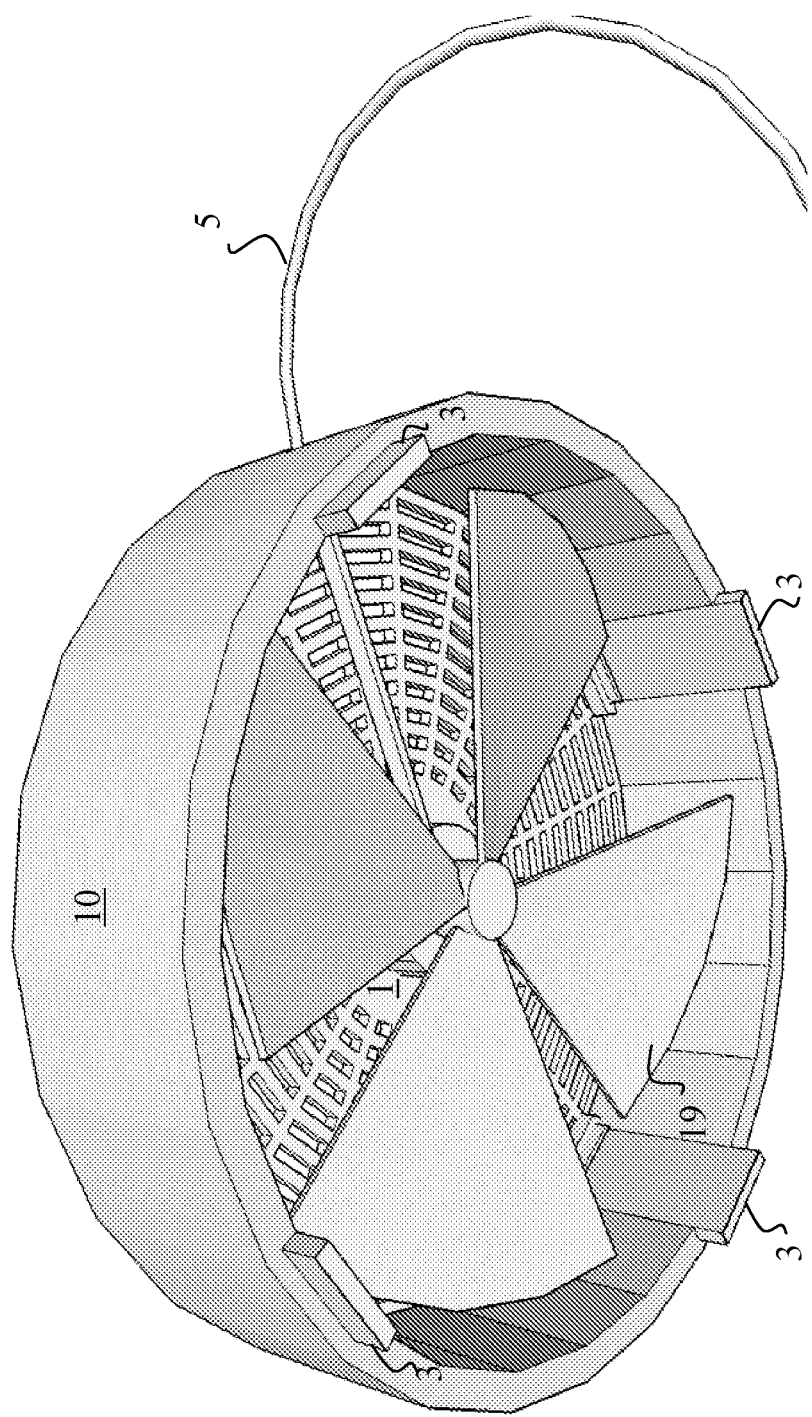
FIG. 3 is a perspective bottom and front view of a blower chamber.
Figure 4:
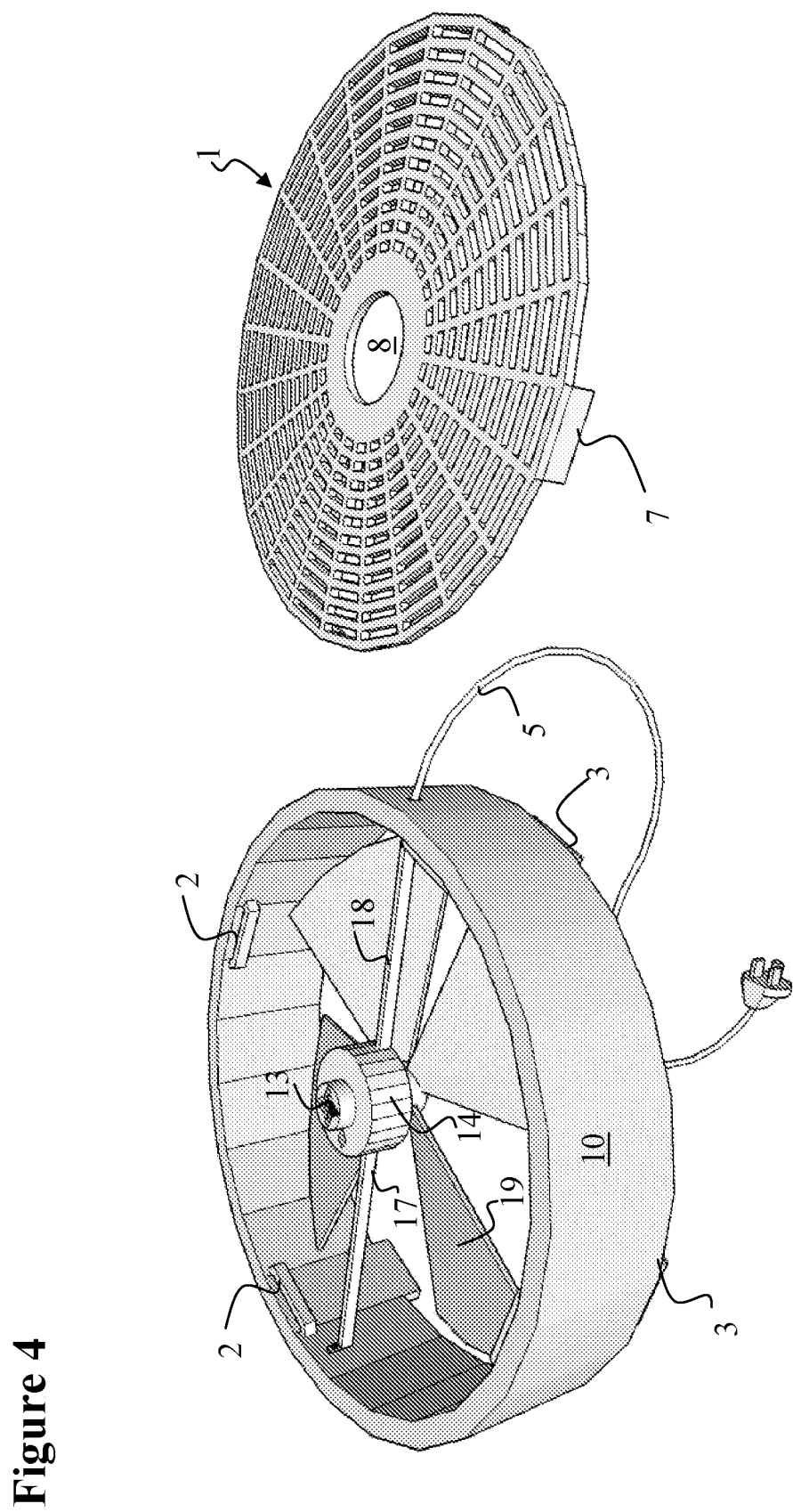
FIG. 4 is a partly exploded perspective top and front view of FIG. 3.
Figure 12:
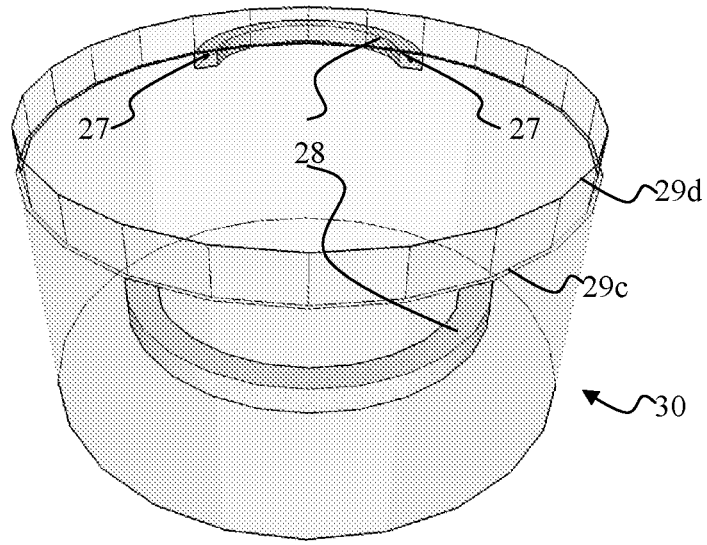
FIG. 12 is a perspective top and side view of the UVC lamp chamber (left side and right side look the same)
Figure 13:
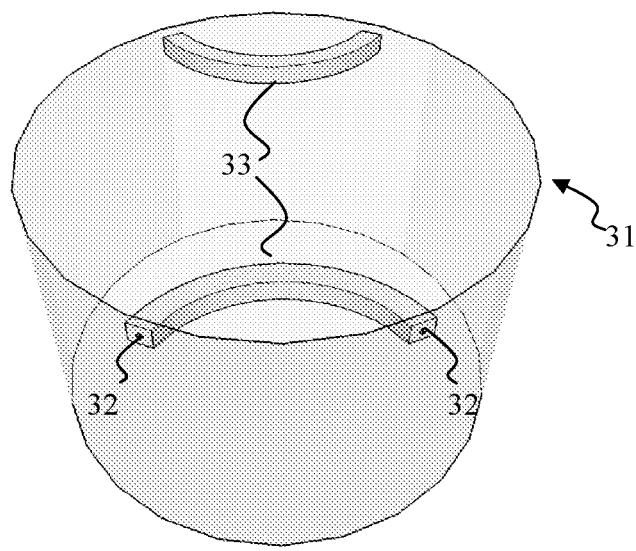
FIG. 13 is a perspective top and side view of the water chamber.
Figure 15:
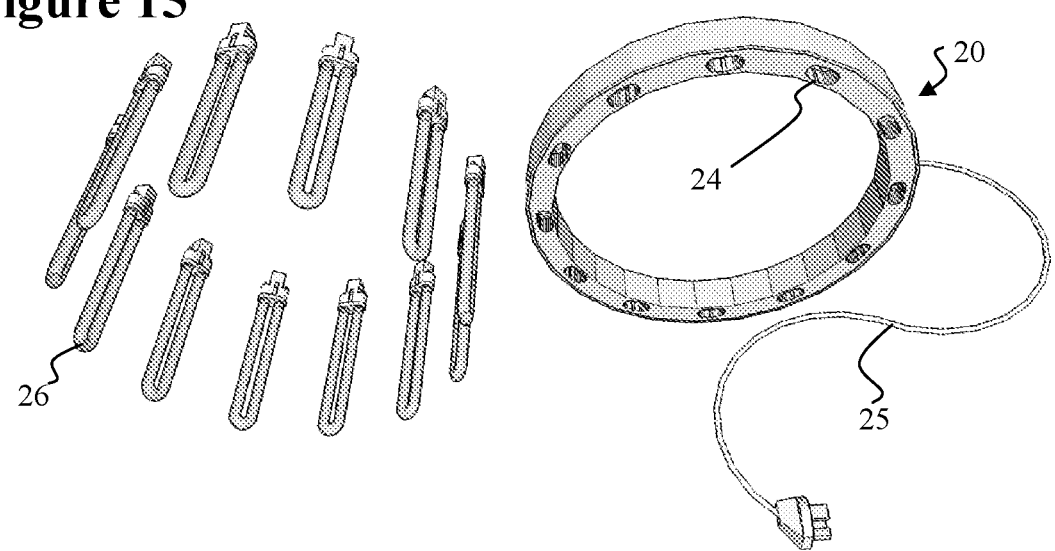
FIG. 15 is an exploded perspective bottom and front view of the UVC lamp holder in FIG. 14.
Figure 26:
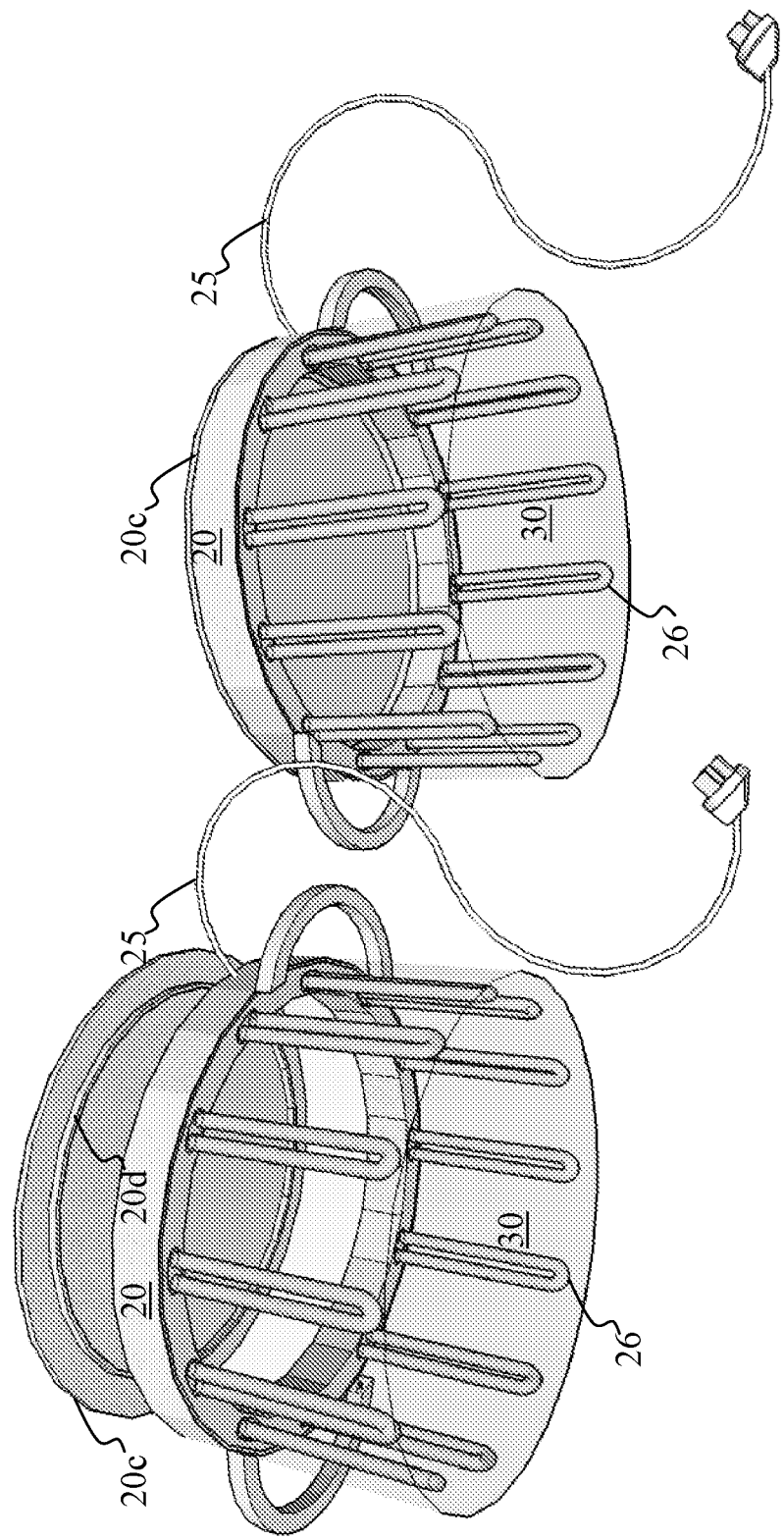
FIG. 26 is a perspective bottom and front view of the UVC lamp chamber, without the water chamber, being closed with a lid to sanitize food, fabric, or utility.
Figure 27:
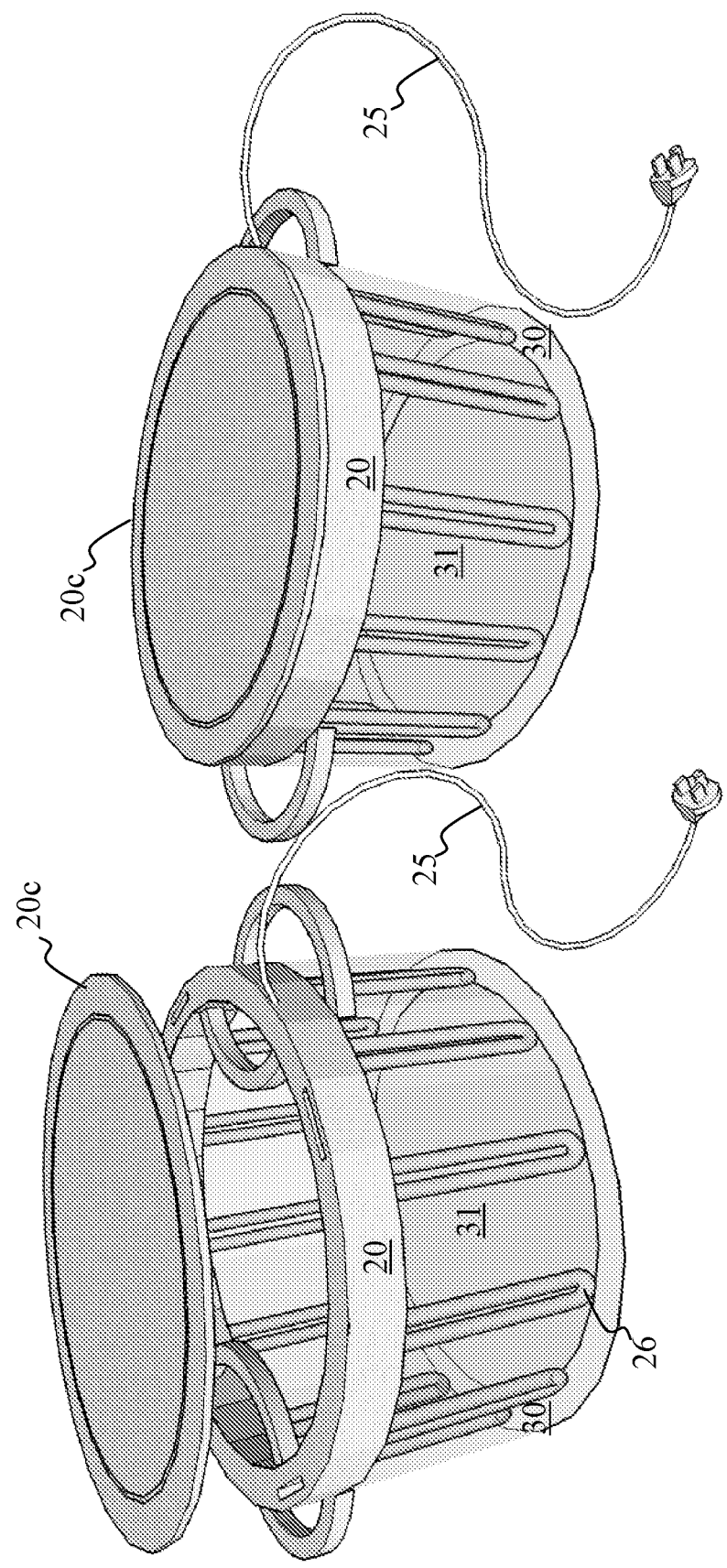
FIG. 27 is a perspective top and front view of the UVC lamp chamber, wherein the water chamber is contained, being closed with a lid to sanitize water or soil.

Referring initially to FIGS. 1-2, an Air-Water-Food-Fabric-Space-Utility sanitizer comprising:
(a) a detachable blower chamber 10 to which a power cord is attached (FIG. 3);
(b) a detachable lamp holder 20 (FIG. 15) to which a power cord and a ballast are attached;
(c) a plurality of UVC lamps 26 (185 nm) (FIG. 15);
(d) a detachable UVC lamp chamber 30 (FIG. 12);
(e) a detachable water chamber 31 (FIG. 13); and
(f) a detachable disk-shaped lid 20c (FIGS. 26-27).

The blower chamber 10, the UVC lamp holder 20, and the UVC lamp chamber 30 are cylindrically shaped and vertically aligned with each other (FIGS. 1-2) while the cylindrically shaped water chamber 31 is coaxially aligned with the UVC lamp chamber 30. All chambers are vertically aligned for the vertical airflow.

Three detachable chambers 10, 30 and 31 house the Air-Water-Food-Fabric-Space-Utility sanitizer (FIG. 1). One power cord (cable and plug) 5 is attached to the blower chamber 10 while the other power cord 25 is attached to the UVC lamp holder 20 (FIG. 1).

Figure 5:
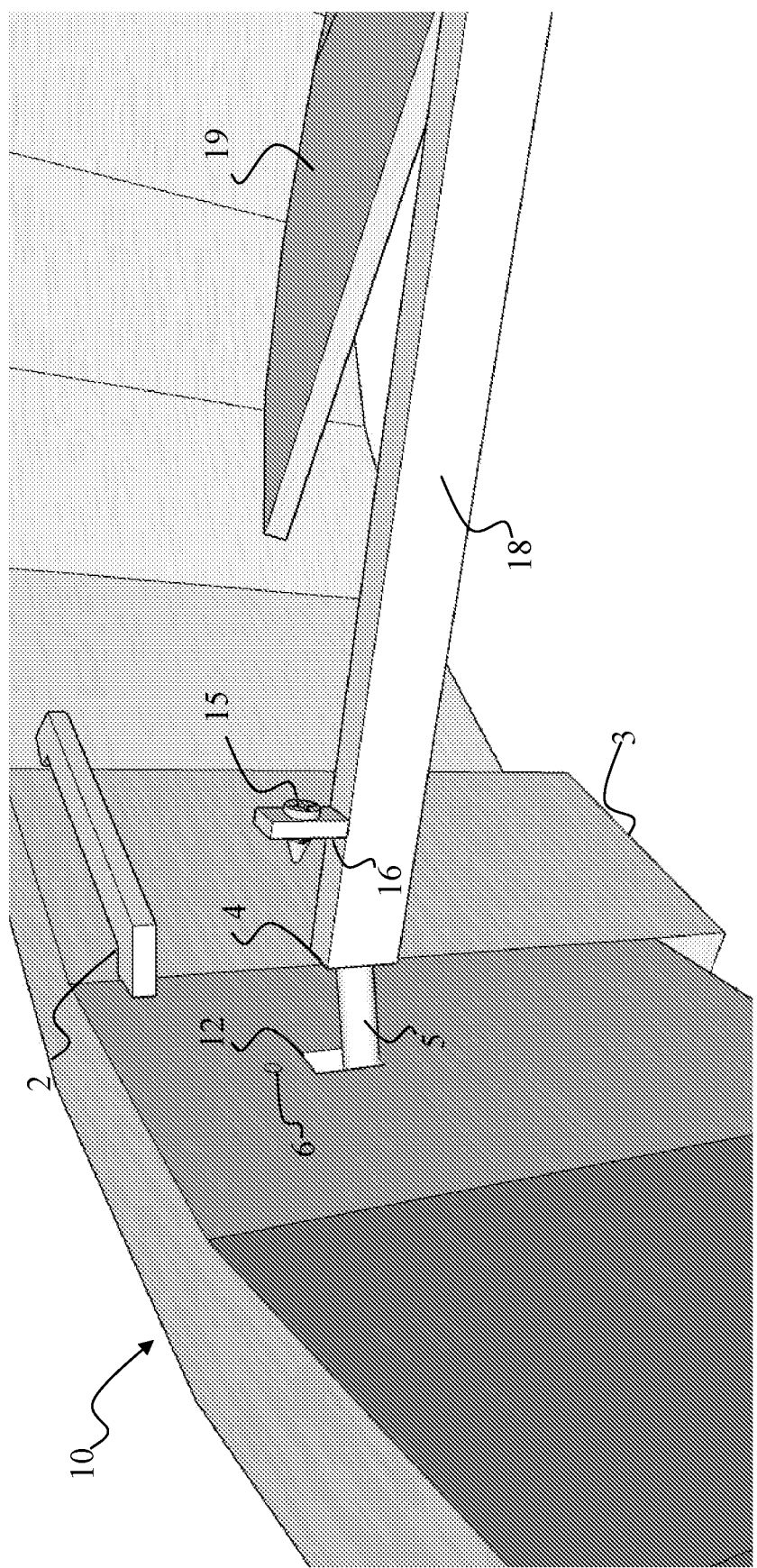
FIG. 5 is a magnified top and rear view, with a partial cut-away, of the blower chamber in FIG. 4, illustrating how a blower motor and its rod are mounted to the blower chamber and how a power cable is connected to the blower motor through a mounting rod.
Figure 6:
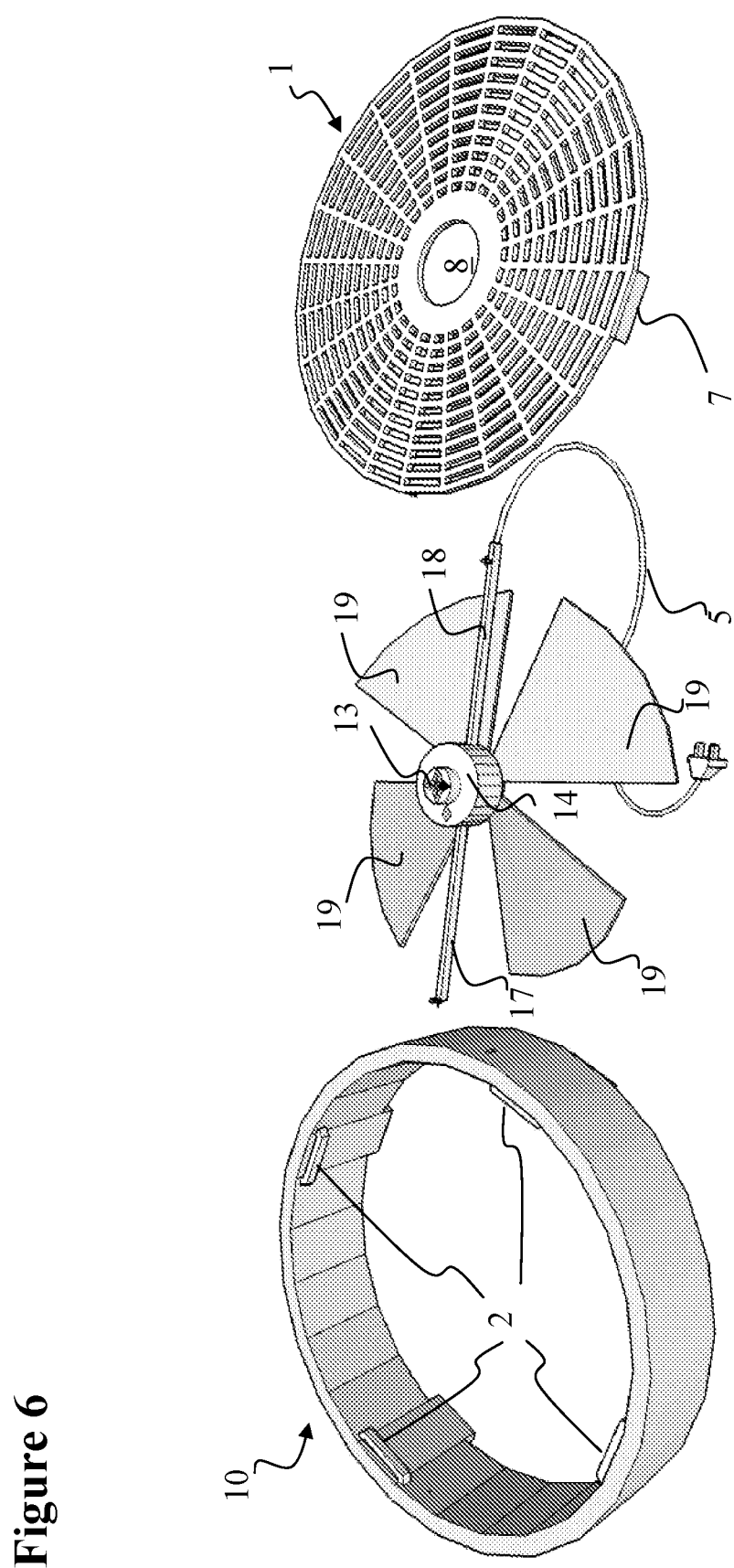
FIG. 6 is an exploded perspective top and front view of the blower chamber in FIG. 3.
Figure 7:
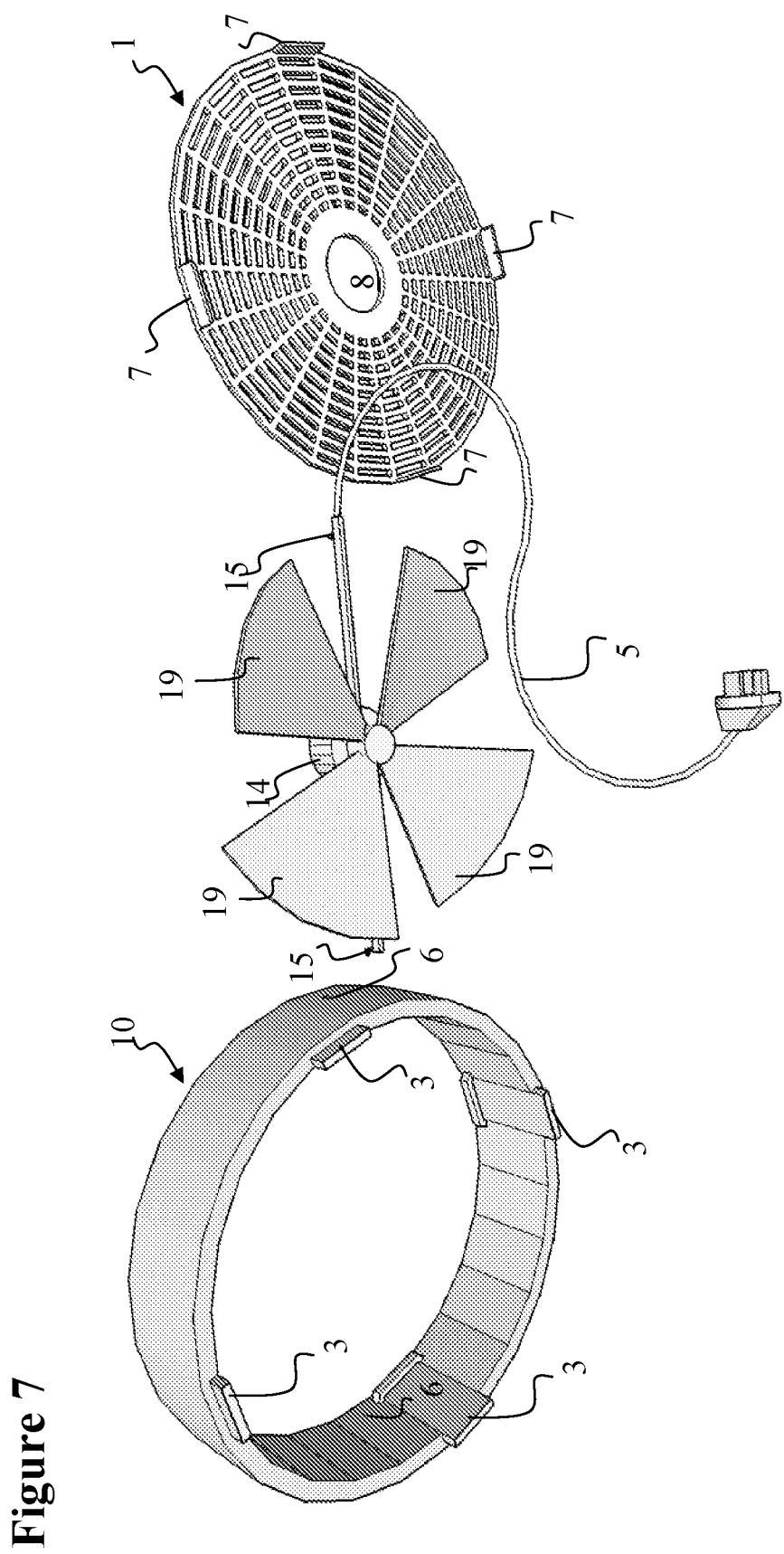
FIG. 7 is an exploded perspective bottom and front view of the blower chamber in FIG. 3.

The blower chamber 10 further comprises an inlet grille 1, a blower 19, a blower motor 14, a motor speed controller 13, and a power cord 5 (FIGS. 3-8). The inlet grille 1 (FIG. 4) is easily attachable to the blower chamber 10 (FIGS. 3-4) by simply inserting four male connectors 7 of the inlet grille 1 into four female connectors 2 of the blower chamber 10 (FIGS. 6-7). The inlet grille (FIG. 4) is also easily detachable by simply pulling it from the top so that users can wash it as often as they can.

Figure 8:
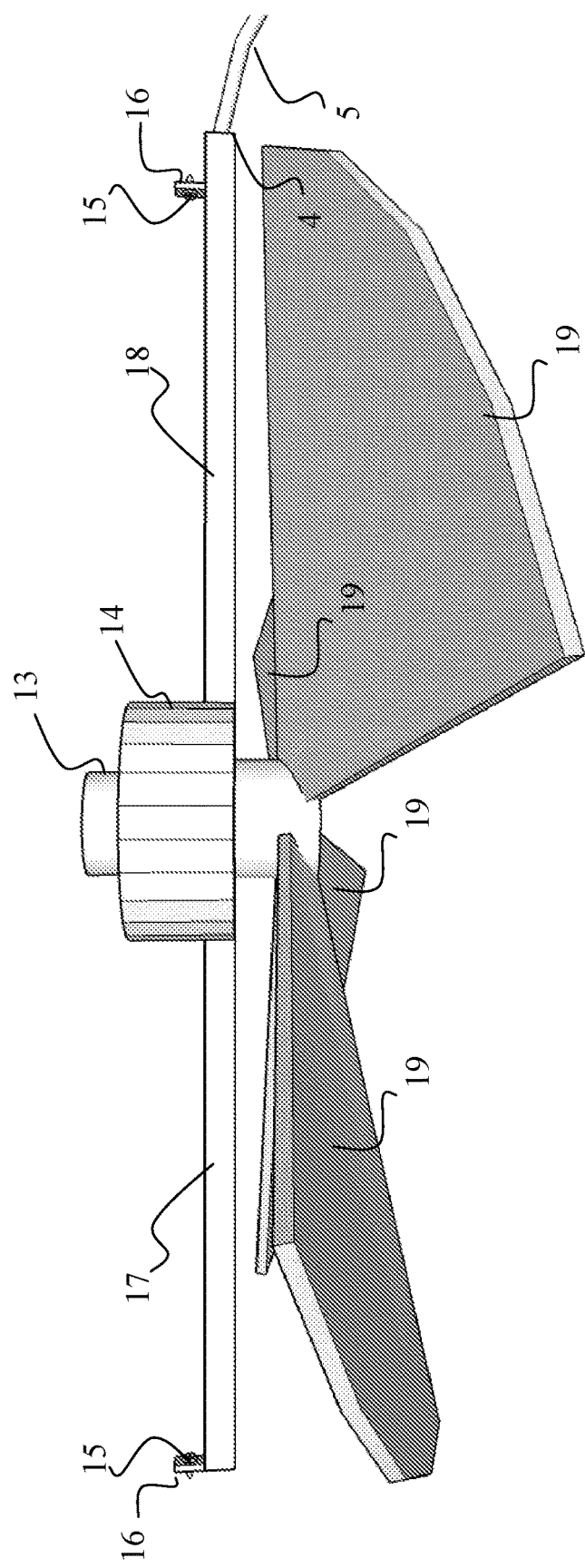
FIG. 8 is an elevational view of a blower in FIG. 7.

A blower motor 14 is horizontally secured by a stainless steel rod 17-18 (FIG. 4) mounted to two holes 6 in the blower chamber 10 by two screws 15 and two brackets 16 (FIGS. 5 and 8).

The rod 18 envelopes a power cable 5 for the blower motor 14 that passes through a rod hole 4 (FIG. 5) to supply power for the blower motor 14. The cable in the rod 18 passes horizontally through a hole 12 (FIG. 5) on the interior wall of the blower chamber 10 so that the power cord 5 can be plugged in a power outlet independently. The rod 17 does not contain any cable (FIG. 8).

The brackets 16 (FIGS. 5 and 8) are composed of stainless steel to avoid UV-induced discoloration. The blower speed is controlled by the motor speed controller 13 that is positioned on the top of the blower motor 14 (FIGS. 6 and 8). The blower speed controller 13 passes vertically through an opening 8 in the inlet grille 1 (FIG. 4) so that the controller 13 (FIG. 4) can emerge from the inlet grille 1 (FIG. 1).

The inlet grille 1 is connected to the blower chamber 10 (FIG. 3) by four male connectors 7 of the inlet grille 1 and by four female connectors 2 of the blower chamber 10 (FIG. 6). Those connectors do not require screws or screwdrivers to disconnect, which makes said invention a detachable apparatus.

Figure 14:
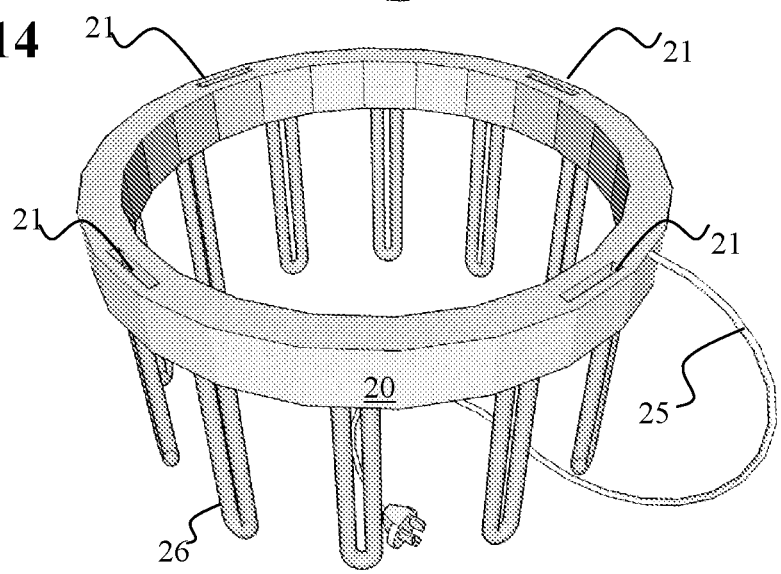
FIG. 14 is a perspective top and front view of the UVC lamp holder (base) to which 12 sockets are mounted.
Figure 21:
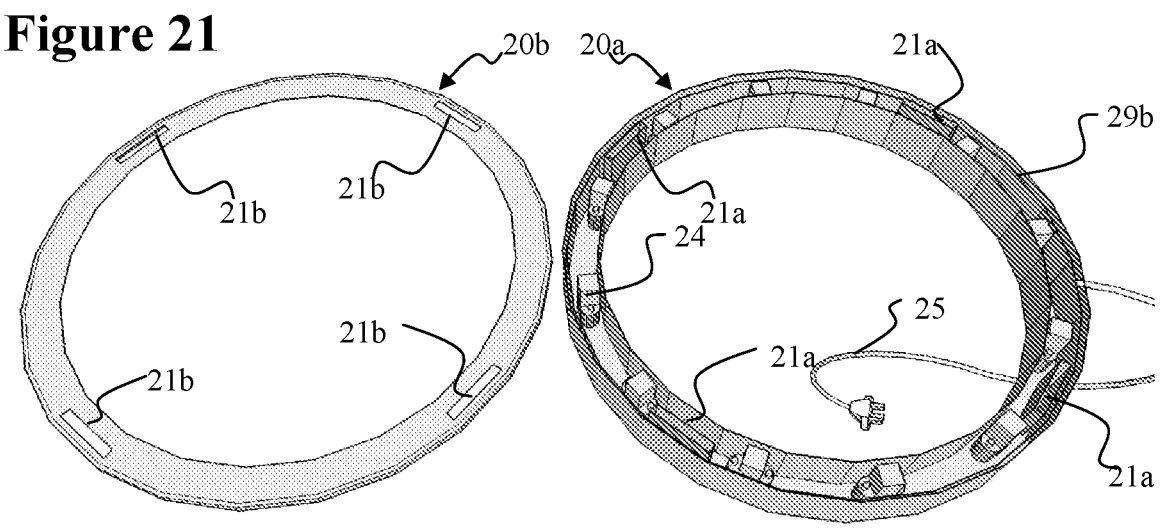
FIG. 21 is a partly exploded perspective top and front view of the UVC lamp holder.

The blower chamber 10 is connected to the UVC lamp holder 20 by four male connectors 3 of the blower chamber 10 (FIG. 7) and by four female connectors 21 (21a and 21b—FIG. 21) of the UVC lamp holder 20 (FIGS. 14 and 21). Those connectors do not require screws or screwdrivers to disconnect either.

The rake angle (35 degree) of the centrifugal fan (FIG. 8) comprising four wide blower blades 19 helps moving the air downwardly into the water chamber 31 so that the blades do not spread the air back into the room. The centrifugal force the propeller creates, throws the air downward by the rake angle. The higher raked propellers can hold and control the air better increasing the thrust downward. 35-degree angle increases the amount of pulling air into the water chamber 31 thereby reducing the time to purify the air. The blades 19 and screws 15 are preferably composed of stainless steel (FIG. 8).

Figure 9:
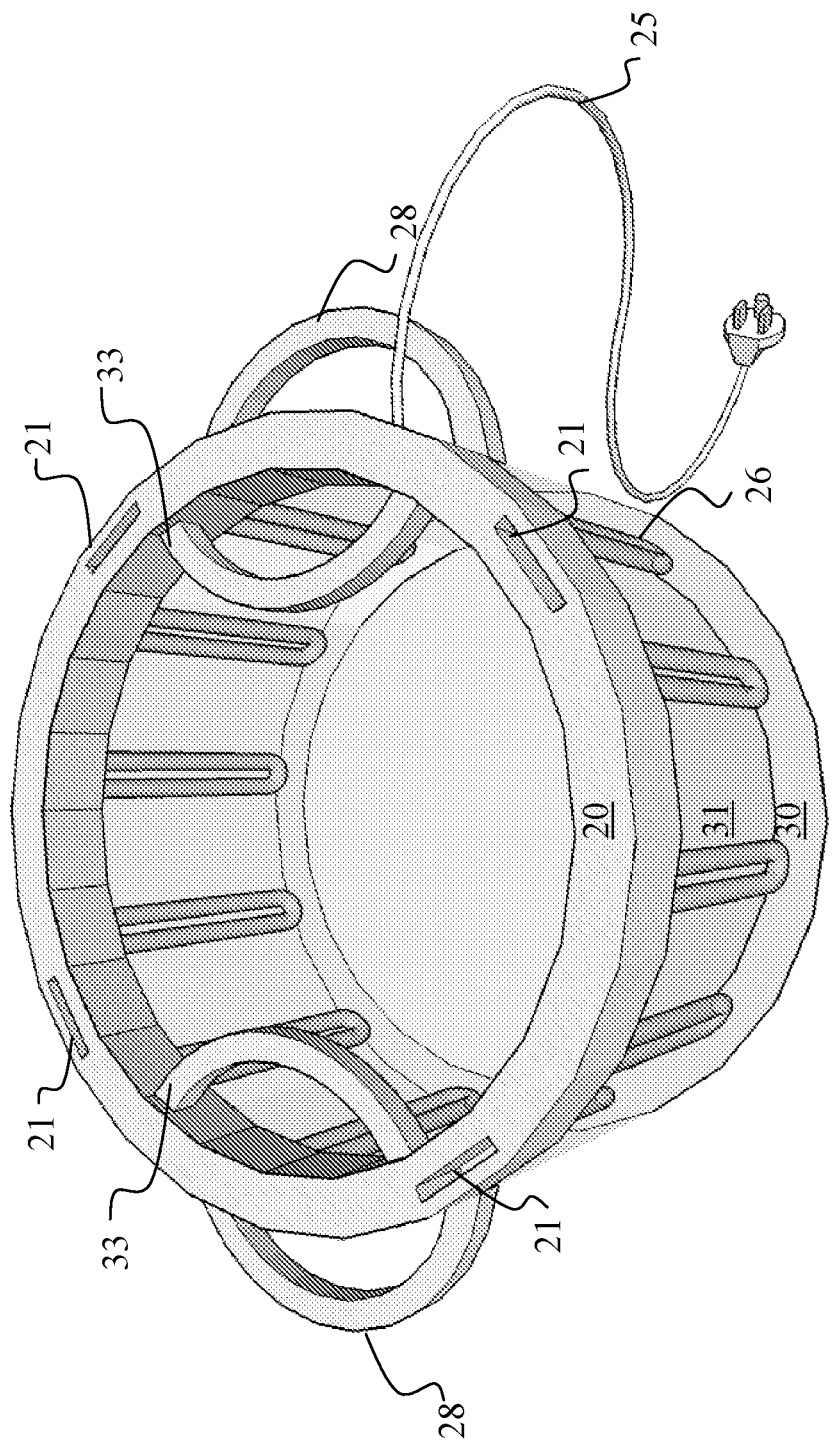
FIG. 9 is a perspective top and front view of a UVC lamp chamber containing a water chamber.
Figure 10:
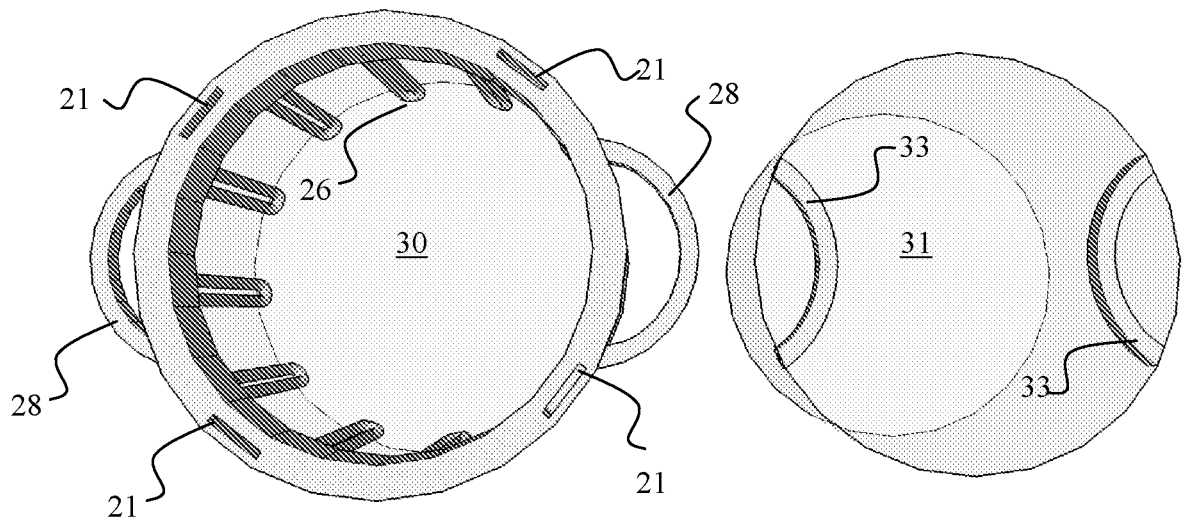
FIG. 10 is a partly exploded perspective top view of FIG. 9, showing the UVC lamp chamber and the water chamber.
Figure 11:
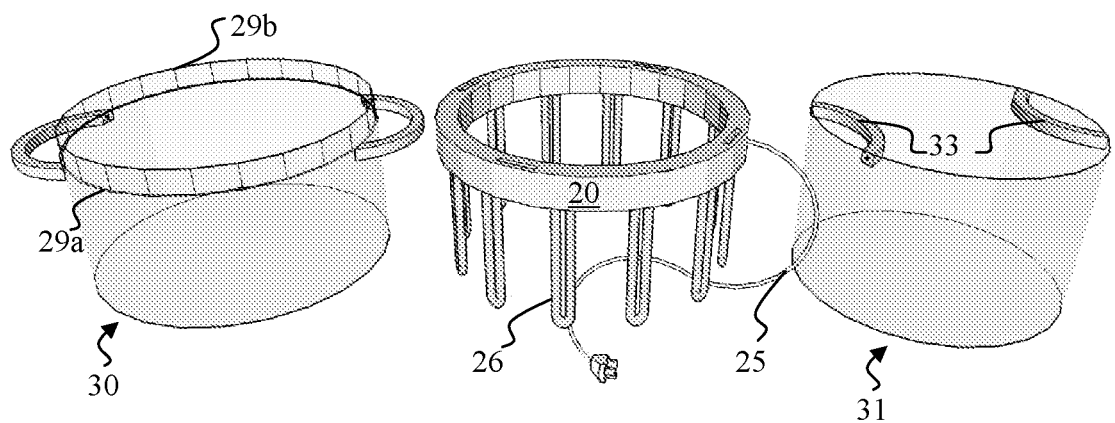
FIG. 11 is an exploded perspective top and front view of FIG. 10, showing the UVC lamp chamber, twelve UVC lamps mounted to a lamp holder, and the water chamber.
Figure 18:
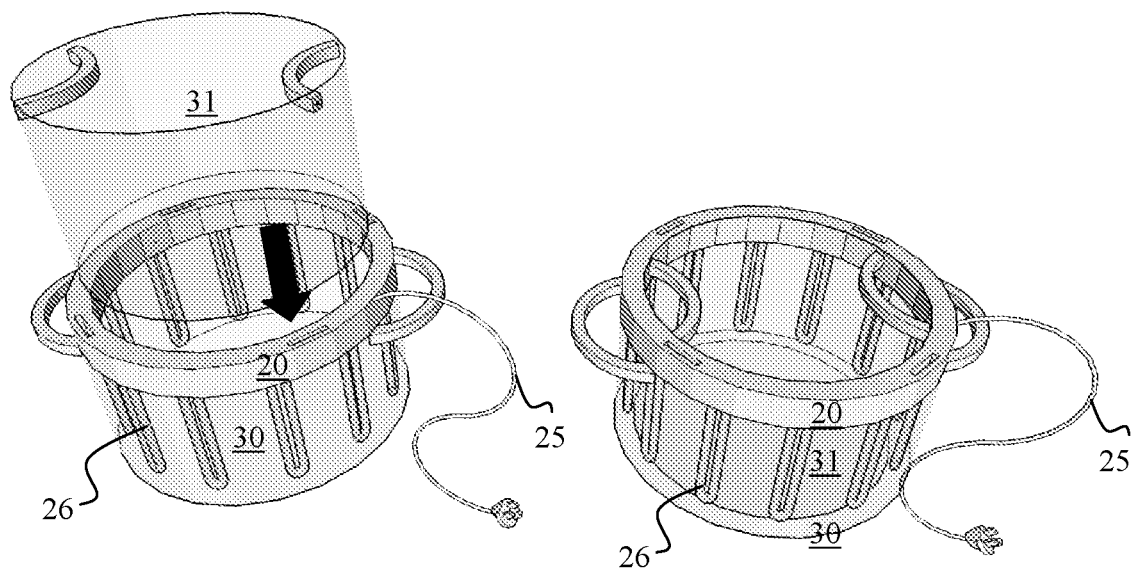
FIG. 18 is a perspective top and front view of the water chamber being vertically inserted into the UVC lamp chamber.

The blower 10 blows the air downwardly (FIG. 1) to the water chamber 31 that is coaxially aligned and contained in the UVC lamp chamber 30 (FIG. 9). The water chamber 31 (FIG. 13) is downwardly inserted into the UV chamber 30 (FIG. 18).

Figure 16:
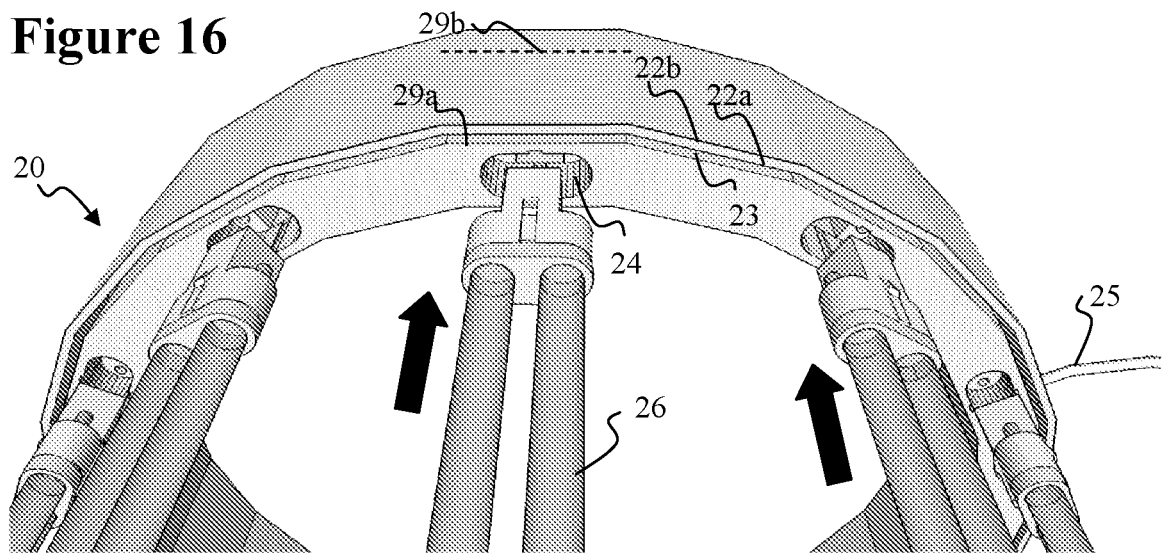
FIG. 16 is a magnified bottom view, with a partial cut-away of FIG. 15.
Figure 19:
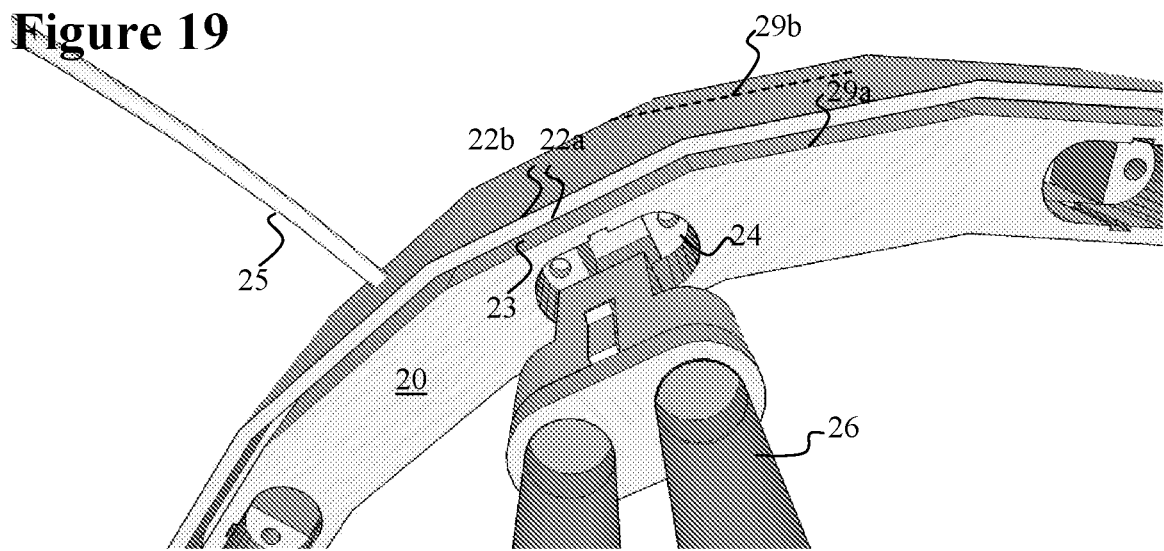
FIG. 19 is a magnified bottom, front and left side view, with a partial cut-away, of the UVC lamp holder in FIG. 16.
Figure 20:
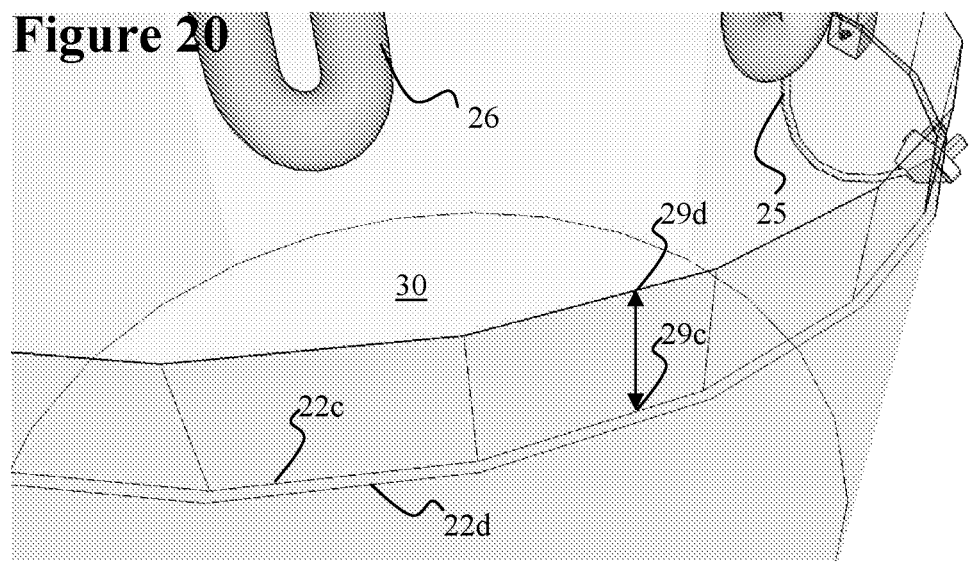
FIG. 20 is a magnified top, front and left side view, with a partial cut-away, of the UVC lamp chamber in FIG. 17.

The UVC lamp holder (base) 20 downwardly docks onto the top of the UVC lamp chamber 30 (FIG. 17), at 29c and 29d (FIG. 20) which were longitudinally marked on the chamber. 22a and 22b were transversely marked on the UVC lamp holder 20 (FIGS. 16 and 19) to indicate where they meet with 22c and 22d which were transversely marked on the UVC chamber 30 (FIG. 20).

The UVC lamp holder 20 has a slot 23 (FIG. 19) to fix its position on the top of the UVC lamp chamber 30 when docking is complete. The top 29d of UVC lamp chamber 30 (quartz glass) (FIG. 20) slides into the slot 23 of the UVC lamp holder (FIG. 19). The slot 23 (from 29a to 29b) in FIG. 19 is as equally deep as the distance between 29c and 29d (FIG. 20) marked on the UVC lamp chamber 30. The slot 23 begins at 22a transversely marked or at 29a longitudinally marked on the UVC lamp holder 20 (FIG. 19).

Figure 17:
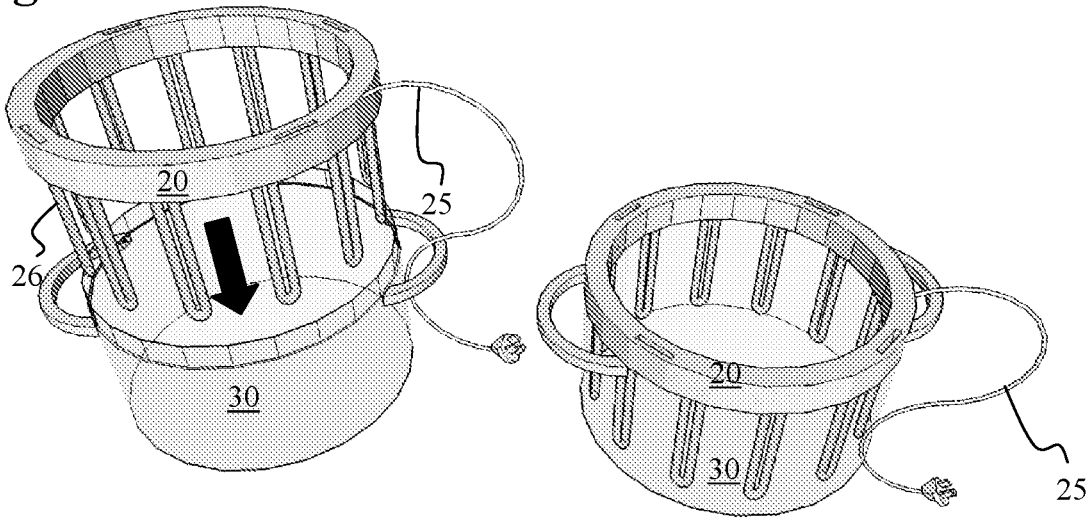
FIG. 17 is a perspective top and front view of the UVC lamp holder vertically docking onto the UVC lamp chamber.

29c and 29d (FIG. 20) were marked on the UVC lamp chamber 30 to indicate where 29a and 29b (FIG. 19) meet with 29c and 29d (FIG. 20) when docking is complete (FIG. 17). 22c and 22d (FIG. 20) were also marked on the UVC lamp chamber 30 to indicate where 22a and 22b (FIG. 19) meet with 22c and 22d (FIG. 20) when docking is complete (FIG. 17).

Figure 22:
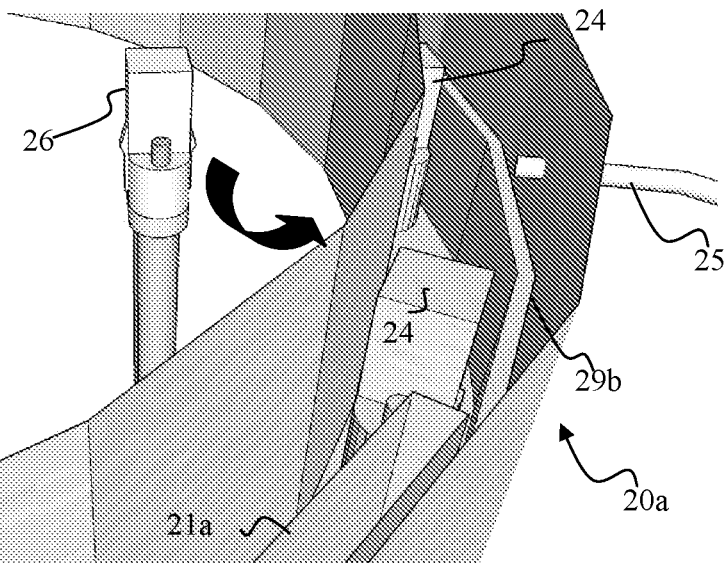
FIG. 22 is a magnified top, front and left side view, with a partial cut-away, of FIG. 21 showing the interior of the UVC lamp holder.
Figure 23:
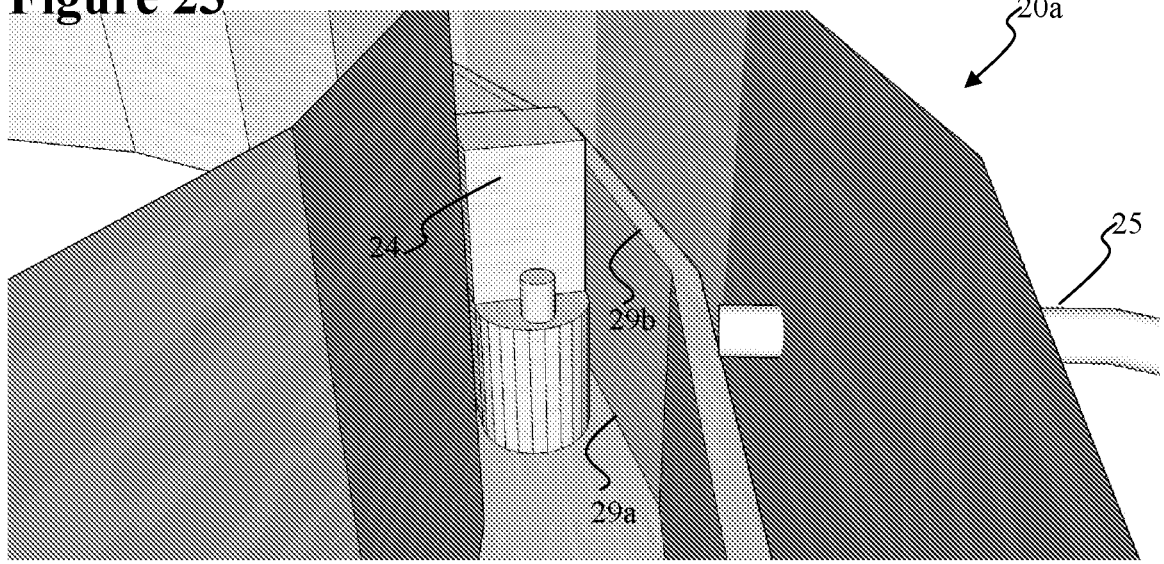
FIG. 23 is a further magnified top, front and left side view, with a partial cut-away, of FIG. 22 showing the interior of the UVC lamp holder.

The UVC lamp holder 20 was exploded to 20a and 20b (FIG. 21). FIGS. 22 and 23 are the details of 20b to show the depth (from 29a to 29b) of the slot 23 in FIG. 19. The power cable 25 is connected to the UVC lamp holder 20 (FIG. 23).

The UVC lamp holder 20 and six (FIG. 25) or twelve (FIG. 24) UVC lamps 26 (185 nm—UVC ozone wavelength—VH fused quartz glass) serve as a stand-style sanitizer (FIGS. 24-25) when they are detached from all chambers 10, 30, and 31.

The maximum capacity to mount UVC lamps 26 is twelve (FIG. 24) and minimum six lamps (FIG. 25) are required. The UVC lamps 26 can be easily removed from the sockets 24 (FIG. 16) for an easy replacement. Unlike many apparatuses, said invention does not require users to open many compartments to reach the UV lamps 26 and it is easy to detect which lamp needs to be replaced or cleaned.

As seen in FIG. 9, a UVC lamp 26 emits UVC photons all around the longitudinal axis thereof. More powerfully, six or twelve of them 26 surround a target placed in the UVC lamp chamber 30 increasing the germicidal power by six to twelve times in all directions (360°). UVC lamps 26 are positioned around the internal wall of the cylindrically shaped UVC lamp chamber 30 to which UVC lamp holder 20 vertically docks (FIG. 9). For the maximum exposure of UVC light, the UVC lamps 26 are vertically mounted to the sockets 24 in the lamp holder 20 (FIGS. 14-15) in accordance with the vertical airflow.

The UVC lamp chamber 30 (FIG. 12) and the water chamber 31 (FIG. 13) are washable since they are made of transparent quartz glass that is capable of transmitting UVC light. The UVC lamp chamber 30 is not coated with a UV-stabilizing material in order to purify the air both inwardly and outwardly from the UVC lamp chamber (FIGS. 1-2).

The detachable UVC lamp chamber 30 (FIG. 12) is coaxially aligned with the water chamber 31 (FIG. 13) in order to utilize the illumination of the UV photons both inwardly and outwardly from the UVC lamp chamber 30. This allows users to utilize the UVC photonic energy outwardly emitted from the UVC lamp chamber (FIG. 9). Unless users are too close to the light, no damage occurs. Likewise, unless the UVC lamps are close (6 inches) enough to the target, the sanitizing effect decreases.

Generally, UVC lamps need a cooling system to offset the high operating heat. However, the heated UVC lamps should not be cooled by a blower since air pressure can shorten the lifespan of UVC lamps. The UVC lamps 26 are cooled by the water in the water chamber 31 at the same time when the water arrests airborne contaminants. The water in the water chamber 31 will offset the heat. Moreover, UVC ray does not generate higher heat than UVB, UVA, or IR ray.

Six or twelve UVC lamps 26 are vertically positioned in the UVC lamp chamber 30 and the water chamber 31 is inserted into the UVC lamp chamber 30 (FIGS. 9 and 18). Therefore, the UVC lamps 26 are not affected by the air pressure from the blower chamber 10 since the UVC lamps 26 are positioned behind the wall of the water chamber that receives the air from the blower 19 (FIGS. 1-2, 9). No airborne contaminants directly touch the UVC lamps in the UVC lamp chamber for the same reason (FIGS. 1-2, 9).

Water in the water chamber 31 converts harmful gas such as formaldehyde ($CH_2O$) to aqueous solution formalin ($CH_4O_2$) that is commonly used as an industrial disinfectant. Gases dissolve in water. Although VH fused quartz UVC lamps (185 nm) alone, without water, can decompose gaseous molecules to gaseous atoms, which is a reason for removal of bad odor and (M)VOCs, water is necessary to arrest gas when the blower has to drive (M)VOC gas into the UVC lamp chamber (FIGS. 1-2). The dissolved liquid is irradiated and poured into a drain in 24 hours.

Both the UVC lamp chamber 30 and the water chamber 31 have handles 28 and 33 on both left and right side of the chambers 30 and 31 so that two hands can safely detach or attach the chambers that are made of quartz glass (96% silica). Quartz glass is capable of transmitting UVC light. The chamber handles 28 and 33 are secured by screws 27 and 32 (FIGS. 12-13) to the walls of the chambers 30 and 31. The handles 28/33 and the screws 27/32 are preferably made of stainless steel since stainless steel is resistant to UV-induced discoloration and water-induced corrosion or rust.

Figure 24:
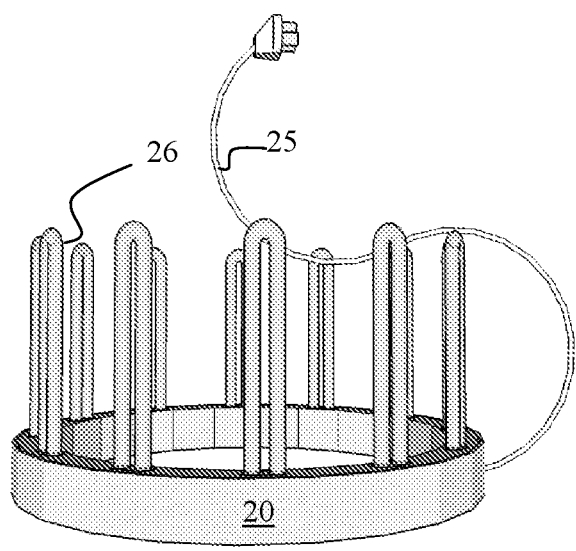
FIG. 24 is a perspective upside down and front view of the UVC lamp holder in FIG. 14 in order to serve as a stand-style sanitizer.
Figure 28:
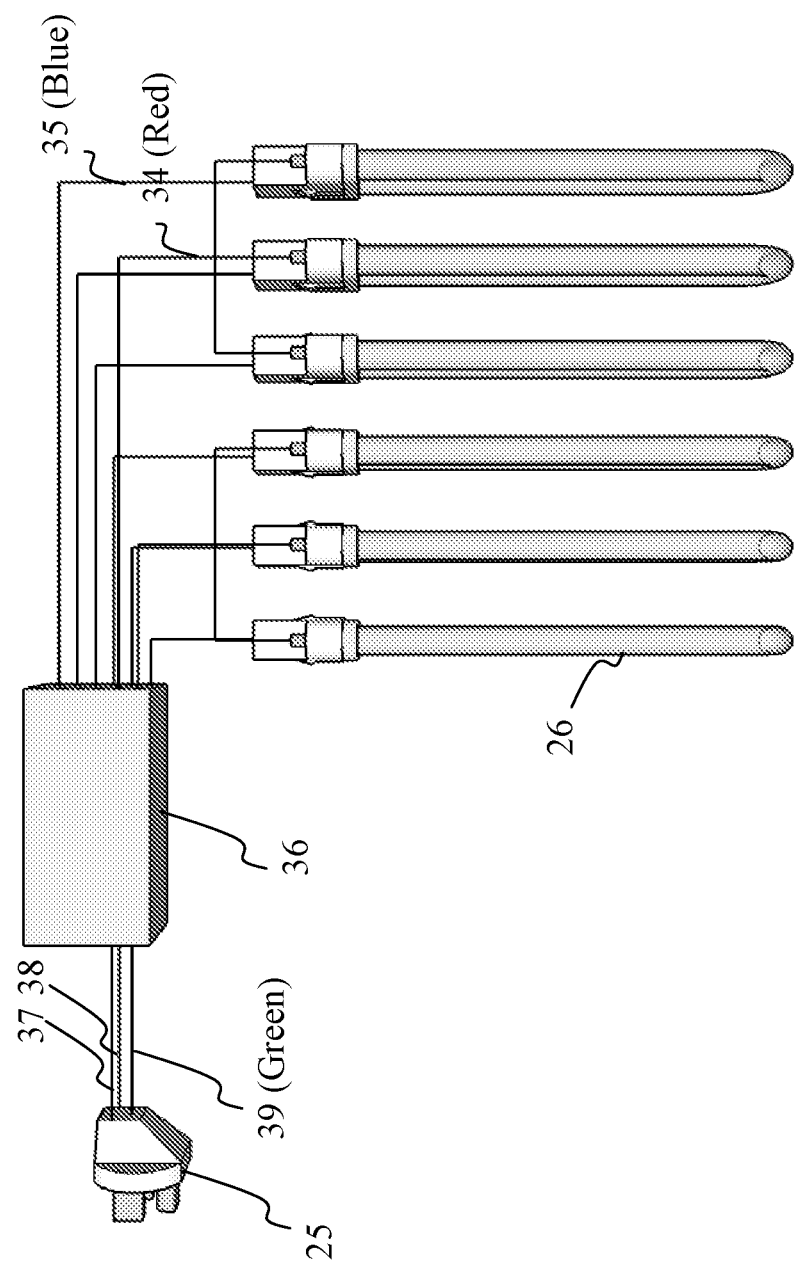
FIG. 28 is an elevational view of six UVC lamps connected to a ballast.
Figure 29:
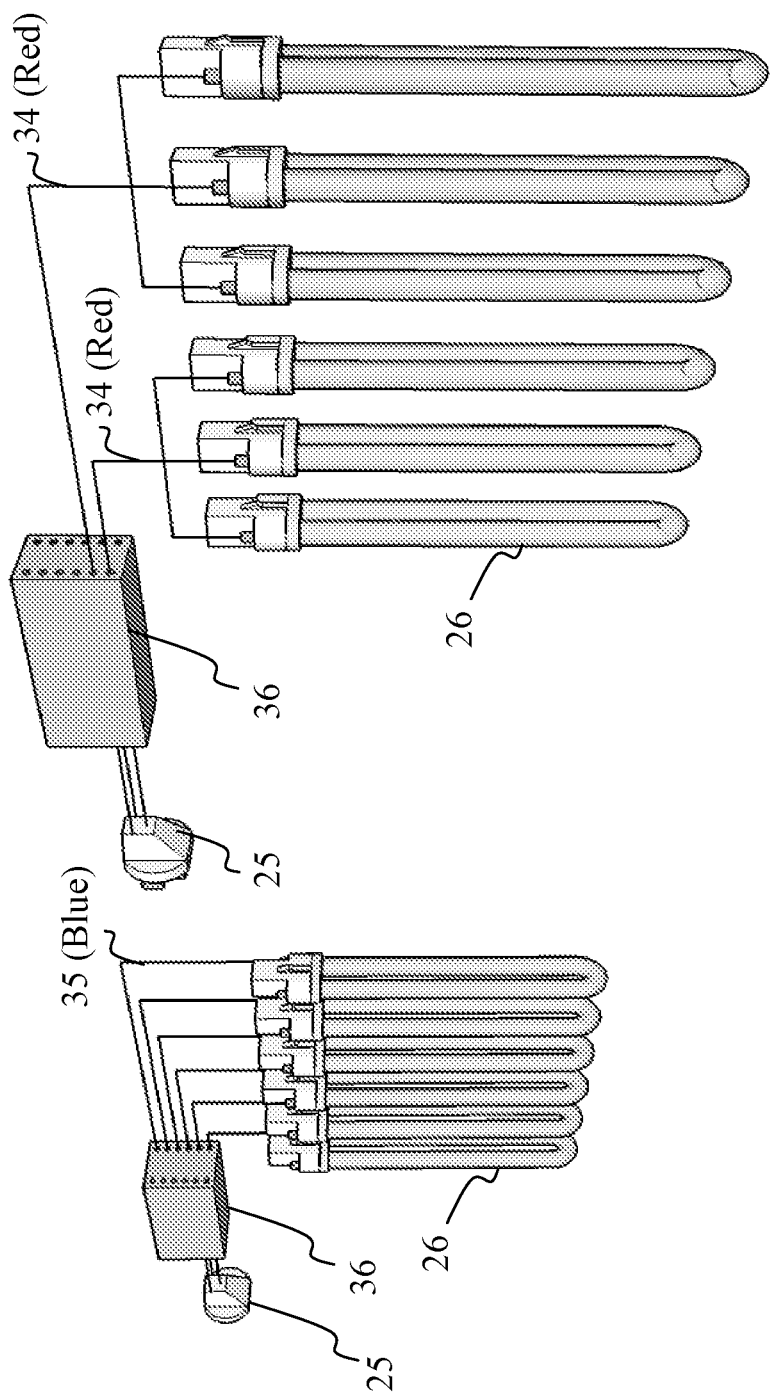
FIG. 29 is a perspective front and left side view of the UVC lamps in FIG. 28, which is duplicated in order to describe how blue wires and red wires are respectively connected to the ballast.

The UVC lamp holder 20 is independently powered through a power cable 25 connected to an electronic ballast 36 (FIGS. 28-29). FIGS. 28 and 29 are an example of parallel connection for the case when six UVC lamps are used. The ballast 36 is connected to the power cord 25 of the UVC lamp holder 20 (FIG. 28), so that users can use it 20 independently when all other compartments are detached therefrom 20 (FIGS. 14 and 24). The parallel connection of red wires 34 and blue wires 35 (FIGS. 28-29) ensures a reliable and safe use of UVC lamps 26. The UVC lamps 26 and the ballast 36 are sold in the market. White (Neutral) 37, Black (Hot) 38, and Green (Ground) 39 wire (FIGS. 28-29) of the ballast 36 are connected to the UVC lamp power cord 25.

Figure 25:
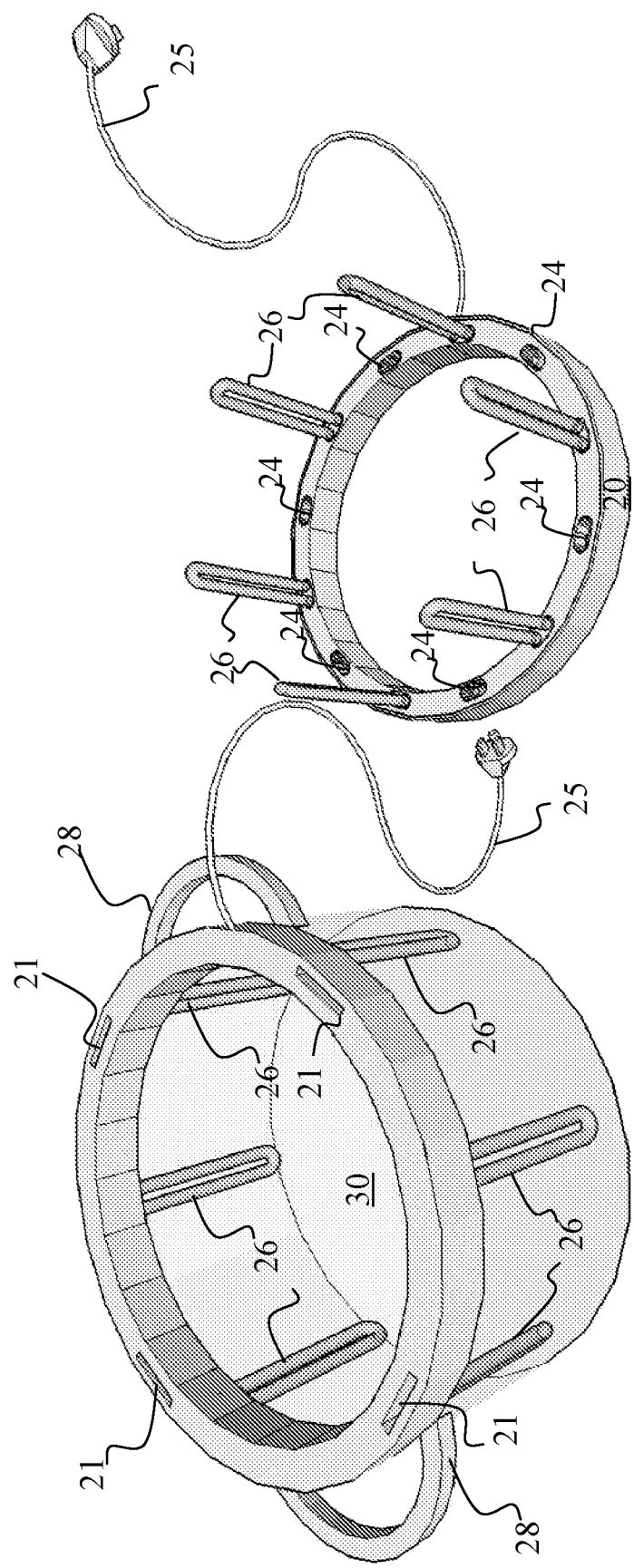
FIG. 25 is a perspective top and front view of an alternative configuration of the plurality of UVC lamps reducing from twelve to six.

By attaching or detaching the chambers 10, 30 and 31, or UVC lamp holder 20 to which UVC lamps 26 are mounted, said invention transforms to an air purifier (FIGS. 1-2), a chamber-style sanitizer (FIGS. 26-27), or a stand-style sanitizer (FIGS. 24-25).

For all purposes described below, if the water chamber 31 is used, users are required to dispose used water by pouring the used water into a drain, wash and refill the water chamber 31 with fresh water in every 24 hours for the best outcome.

To serve as an air purifier (FIGS. 1-2), the water chamber 31 is inserted into the UVC lamp chamber 30 (FIG. 18). Users can fill the water chamber 31 with water (⅓ of the capacity when UVC lamps are used, ⅔ of the capacity when oxidized water is used). If UVC light is used, users must supply power for the UVC lamps 26 via the power cord 25 of the UVC lamp holder 20. If an oxidizer such as hydrogen peroxide or sodium hypochlorite (bleach) is used, users must unplug the power cord 25. Whether the UVC light is used or not, users should supply power for the blower motor 14 via the power cord 5 of the blower chamber 31 (FIG. 1).

As an air purifier (FIGS. 1-2), to destroy pathogenic spores, said invention provides two alternative methods below.
(a) Using the UVC lamps and water:
The UVC lamps 26 are capable of producing ozone. The blower 19 in the blower chamber 10 drives airborne contaminants into the water chamber 31. Once they arrive at the water chamber 31, the water is irradiated by six or twelve UVC lamps 26. Water arrests contaminants and inhibits spore dispersal. The UVC lamps 26 are positioned inside the UVC lamp chamber 30, and destroy pathogens (FIGS. 1-2).
(b) Using oxidized water:
The power cord 25 for the UVC lamps 26 is unplugged. The blower 19 drives airborne contaminants into the water chamber 31. Once they arrive at the water chamber 31, oxidized water (diluted hydrogen peroxide or diluted sodium hypochlorite) arrests pathogens and destroys them (FIGS. 1-2).

As an air purifier (FIGS. 1-2), to remove small particles such as dust, dust mites, and pollen in the air, the blower 19 in the blower chamber 10 drives them into the water chamber 31 which should be emptied and refilled with fresh water later.

As an air purifier (FIGS. 1-2), to remove (M)VOC gas such as aldehyde, formaldehyde, alcohols, and hydrocarbon in the air, the blower drives gas into the water chamber wherein water converts gaseous molecules to aqueous molecules.

As an air purifier (FIGS. 1-2), to remove cigarette smoke (acrolein, $C_3H_4O$), the blower in the blow chamber drives smoke into the water chamber. Acrolein from smoke is water-soluble.

To serve as a chamber-style sanitizer, the blower chamber 10 and the water chamber 31 are detached (FIG. 26) and the UVC lamp chamber (FIG. 12) is used to sanitize food (meats, washed vegetables, fruits, etc.), fabric (masks, towels, gloves, hats, baby clothes, etc.), or small household utility (pacifier, silverware, etc.). Pests and parasites in meats or plants are also destroyed during the irradiation process.

As a chamber-style sanitizer (FIG. 26), the UVC lamp chamber 30 (FIG. 12) is closed with the lid 20c and power is supplied for the UVC lamps 26 using the power cord 25. The vertically positioned UVC lamps sanitize the targets inside the UVC lamp chamber 30 wherein the targets receive UVC light from all directions (360°) since the UVC lamps 26 surround the targets placed in the center of the UVC lamp chamber 30.

As a chamber-style sanitizer (FIG. 26), the lid 20c is fixed in a position inside the UVC lamp chamber 30 by a rim 20d of the lid 20c that fits within the diameter of the UVC lamp holder 20 docked onto the UVC lamp chamber 30. The lid protects the chambers 30 and 31 from insects and airborne contaminants during the irradiation process. The lid is preferably formed of stainless steel to reflect the light within the UVC lamp chamber 30 and to prevent UV-induced discoloration.

As a chamber-style sanitizer (FIG. 9), if users leave the UVC lamp chamber 30 open to the air by detaching the lid 20c, insects such as mosquitoes, flies, and mosses are drawn thereto 30 and die therein 30. The glass-made chambers are washable after use.

As a chamber-style sanitizer (FIG. 27), the water chamber 31 is vertically inserted into the UVC lamp chamber 30 (FIG. 18) to purify water for drinking. The UVC lamp chamber 30, wherein the water chamber 31 is contained, is closed with the lid 20c during the irradiation process (FIG. 27). The water is irradiated by the UVC lamps 26 positioned inside the UVC lamp chamber 30 (FIG. 27). Although UVC lamp chamber 30 can be used without the water chamber (FIG. 26), the water chamber is necessary to protect UVC lamps from water damages. The water receives UVC light from all directions (360°) since the UVC lamps surround the water in the water chamber, which makes said invention unique from all prior apparatuses.

As a chamber-style sanitizer, the water chamber 31 is vertically inserted into the UVC lamp chamber 30 (FIG. 18) to purify infected soil. The water chamber 31 is filled with the targeted soil. The UVC lamp chamber 30, wherein the water chamber 31 is contained, is closed with the lid 20c during the irradiation process (FIG. 27).

To serve as a stand-style sanitizer (FIG. 24), all chambers 10, 30, and 31 are detached. By detaching all three chambers, said invention transforms to a stand-style sanitizer (FIG. 24).

As a stand-style sanitizer (FIG. 24), it sanitizes or deodorizes space. Users can turn the UVC lamp holder 20 to which UVC lamps 26 are mounted, upside down and place it 20 inside kitchen cabinets, shoe cabinets, dressers, wardrobes, closets, bathrooms, shower rooms, baby cribs, toilet rooms, bedrooms, trash areas, traveler's bags, drawers, storage, boxes, surgery rooms, etc.

As a stand-style sanitizer (FIG. 24), it also develops germination of seeds if a UV transmittable seedling starter is placed in the center thereof (FIG. 24).

While the form of apparatus described constitutes the preferred embodiment of this invention, it is to be understood that the invention is not limited to this precise form of apparatus, and the changes may be made therein without departing from the scope of the invention which is defined in the appended claims.

The invention claimed is:
1. An Air-Water-Food-Fabric-Space-Utility sanitizer comprising:
   (a) a detachable blower chamber, containing a blower, to which a power cord is attached;
   (b) a detachable UVC lamp holder to which a power cord and a ballast are attached;
   (c) a plurality of UVC lamps;
   (d) a detachable UVC lamp chamber;
   (e) a detachable water chamber; and
   (f) a detachable disk-shaped lid;
   and wherein the Air-Water-Food-Fabric-Space-Utility sanitizer is configured to be transformable into differing sanitizer configurations when said detachable UVC lamp holder, detachable UVC lamp chamber, detachable water chamber, and/or detachable disk-shaped lid are used together and/or detached from each other without requiring a filter or an air outlet by using either UVC-irradiated water or oxidized water as a filter or as a pathogen killer.

2. The Air-Water-Food-Fabric-Space-Utility sanitizer of claim 1, wherein said detachable blower chamber, said detachable lamp holder, said detachable UVC lamp chamber, and said detachable water chamber are cylindrically shaped; and coaxially aligned with an inlet airflow.

3. The Air-Water-Food-Fabric-Space-Utility sanitizer of claim 1, wherein said detachable blower chamber and said detachable lamp holder are vertically aligned with said detachable UVC lamp chamber wherein UVC lamps surround a target to sanitize.

4. The Air-Water-Food-Fabric-Space-Utility sanitizer of claim 1, wherein said detachable lid covers both said detachable water chamber and said detachable UVC lamp chamber when said invention serves as a chamber-style sanitizer.

5. The detachable UVC lamp holder of claim 1, further comprising:
 (a) a cylindrically shaped stainless steel housing;
 (b) a cylindrically shaped stainless steel lid through which four male connectors of said blower chamber of claim 1 pass;
 (c) four female connectors;
 (d) a slot on the bottom to vertically dock onto said UVC lamp chamber of claim 1;
 (e) twelve sockets mounted thereto; and
 (f) a power cord connected to a motor-mounting rod and said ballast of claim 1 to serve as a stand-style sanitizer when said UVC lamps of claim 1 are mounted thereto.

6. The detachable UVC lamp chamber of claim 1; wherein the UVC lamp chamber has the following characteristics (a) composed of UV transmittable quartz glass; (b) coaxially aligned with said water chamber of claim 1; (c) vertically aligned with said blower chamber and said UVC lamp holder of claim 1; (d) having two stainless steel handles outwardly mounted to the external wall thereof; (e) a slot for docking of said UVC lamp holder; (f) supporting said UVC lamp holder and said blower chamber of claim 1; (g) containing said water chamber when purifying air, water, or soil; (h) housing UVC lamps of claim 1 after said UVC lamp holder to which UVC lamps are mounted, docks vertically thereto; (i) being a container as a chamber-style sanitizer; and (j) being a container for killed insects after flying or floating insects are drawn thereto.

7. The detachable water chamber of claim 1, wherein the detachable water chamber has the following characteristics (a) composed of UVC transmittable quartz glass; (b) coaxially aligned with said UVC lamp chamber of claim 1; (c) vertically aligned with said blower chamber and said UVC lamp holder of claim 1; (d) having two stainless steel handles inwardly mounted to the interior wall thereof; (e) being a container for oxidized or irradiated water to destroy airborne contaminants; (f) being a container for water to convert harmful gas to liquid; (g) being a container for water to arrest particles; (h) being a container for drinking water to purify; and (i) being a container for infected soil to destroy soil contaminants.

8. The detachable blower chamber of claim 1, further comprising: (a) an inlet grille composed of stainless steel; (b) four male connectors on the bottom of said inlet grille to connect with said blower chamber; (c) four female connectors on the top of said blower chamber to connect with said inlet grille; (d) four male connectors on the bottom of said blower chamber to connect with four female connectors of said UVC lamp holder of claim 1; (e) a motor for driving a centrifugal fan in rotation; (f) a centrifugal fan with 35-degree rake angle to downwardly drive airborne contaminants into said water chamber of claim 1; (g) a blower speed controller appearing above said inlet grille while said controller is positioned under said inlet grille; and (h) a motor-mounting rod enveloping a power cable connected to a plug.

\* \* \* \* \*